(12) United States Patent
Johncock et al.

(10) Patent No.: US 11,723,850 B2
(45) Date of Patent: Aug. 15, 2023

(54) LIQUID AND TRANSPARENT BLEND OF UV FILTERS

(71) Applicant: SYMRISE AG, Holzminden (DE)

(72) Inventors: William Johncock, Reinbek (DE); Jürgen Claus, Bevern (DE)

(73) Assignee: Symrise, AG, Holzminden (DE)

( * ) Notice: Subject to any disclaimer, the term of this patent is extended or adjusted under 35 U.S.C. 154(b) by 0 days.

(21) Appl. No.: 17/289,294

(22) PCT Filed: Nov. 2, 2018

(86) PCT No.: PCT/EP2018/080037
§ 371 (c)(1),
(2) Date: Apr. 28, 2021

(87) PCT Pub. No.: WO2020/088778
PCT Pub. Date: May 7, 2020

(65) Prior Publication Data
US 2022/0071872 A1    Mar. 10, 2022

(51) Int. Cl.
| | |
|---|---|
| *A61K 8/35* | (2006.01) |
| *A61K 8/06* | (2006.01) |
| *A61K 8/27* | (2006.01) |
| *A61K 8/29* | (2006.01) |
| *A61K 8/34* | (2006.01) |
| *A61K 8/37* | (2006.01) |
| *A61K 8/49* | (2006.01) |
| *A61Q 17/04* | (2006.01) |

(52) U.S. Cl.
CPC .............. *A61K 8/35* (2013.01); *A61K 8/062* (2013.01); *A61K 8/064* (2013.01); *A61K 8/27* (2013.01); *A61K 8/29* (2013.01); *A61K 8/347* (2013.01); *A61K 8/37* (2013.01); *A61K 8/4966* (2013.01); *A61Q 17/04* (2013.01); *A61K 2800/262* (2013.01); *A61K 2800/43* (2013.01); *A61K 2800/51* (2013.01); *A61K 2800/522* (2013.01); *A61K 2800/524* (2013.01); *A61K 2800/5922* (2013.01); *A61K 2800/805* (2013.01); *A61K 2800/87* (2013.01)

(58) Field of Classification Search
None
See application file for complete search history.

(56) References Cited

U.S. PATENT DOCUMENTS

2018/0168970 A1* 6/2018 Makarovsky .......... A61Q 17/04

FOREIGN PATENT DOCUMENTS

| DE | 10 2005 059742 A1 | 6/2007 | |
|---|---|---|---|
| DE | 20 2013 103395 U1 | 8/2013 | |
| EP | 2921157 A1 * | 9/2015 | ............. A61K 33/08 |
| KR | 101 798 024 B1 | 11/2017 | |
| WO | 2016/201260 A1 | 12/2016 | |
| WO | 2018/198800 A1 | 11/2018 | |

* cited by examiner

*Primary Examiner* — Nannette Holloman
(74) *Attorney, Agent, or Firm* — Dilworth & Barrese, LLP

(57) ABSTRACT

Suggested is a liquid and transparent blend of UV filters, comprising, consisting or essentially consisting of (a) at least one solid UVA filter dissolved in (b) at least one liquid UVB filter exhibiting a linear UV absorbance curve with a variance of +/−10% in the range of 290 to 360 nm as measured from a solution containing 10 mg/l of said mixture in ethanol, wherein said solid UVA filters are selected from the group consisting of Avobenzone, Bemotrizinol and mixtures thereof.

22 Claims, 1 Drawing Sheet

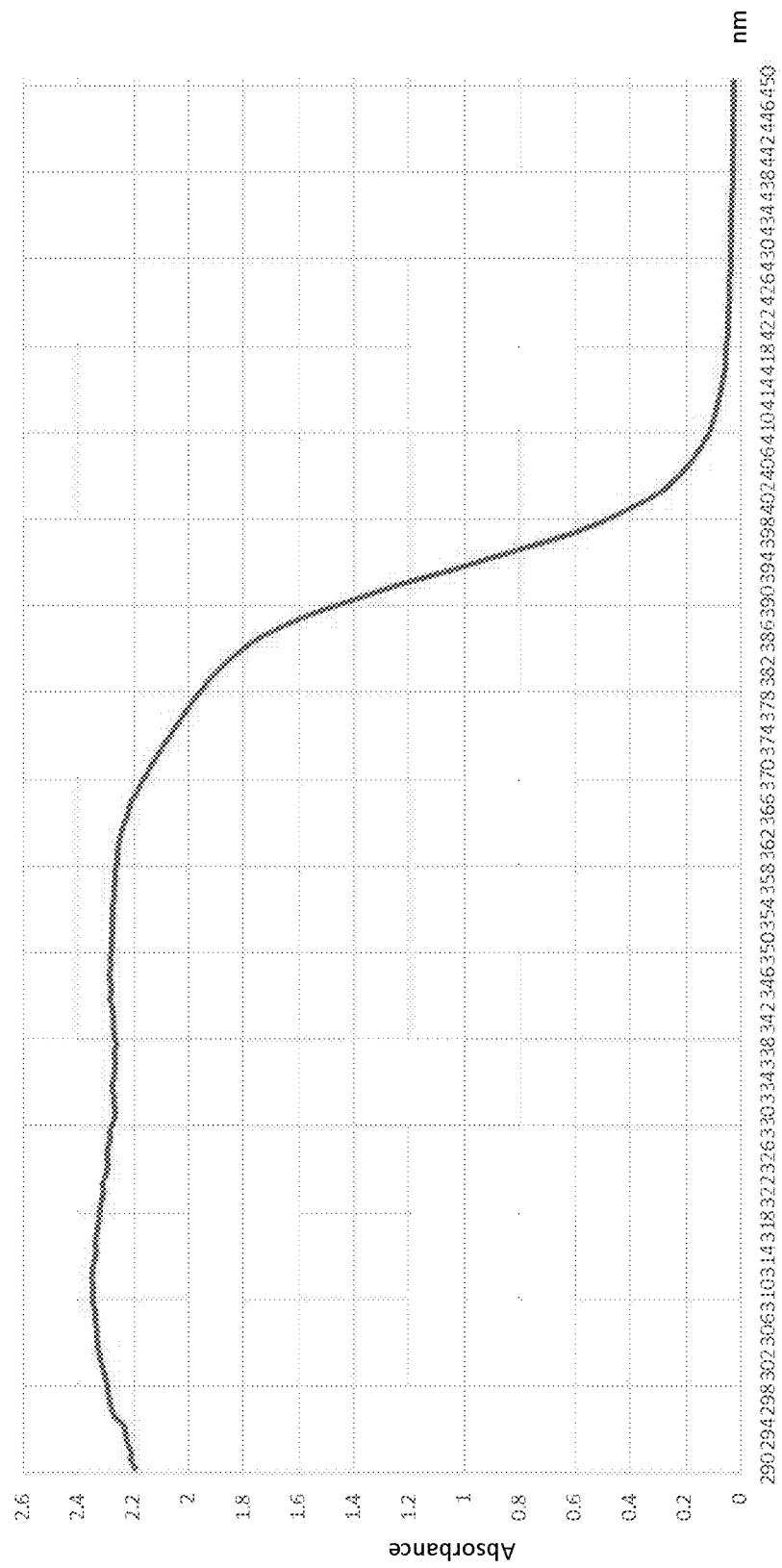

LIQUID AND TRANSPARENT BLEND OF UV FILTERS

AREA OF INVENTION

The present invention refers to the area of sun care products and refers to a specific blend of solid UVA-filters in liquid UVB-filters and compositions comprising these blends.

BACKGROUND OF THE INVENTION

UV absorbers are compounds which have a pronounced absorption capacity for ultraviolet radiation. They are used in particular as sunscreens in cosmetic, dermatological and pharmacological preparations, but also to improve the light fastness of industrial products, such as paints, varnishes, plastics, textiles, polymers such as, for example, polymers and copolymers of mono- and di-olefins, polystyrenes, polyurethanes, polyamides, polyesters, polyureas and polycarbonates, packaging materials and rubbers.

UV rays are classified according to their wavelength as UVA rays (320-400 nm, UVA-I: 340-400 nm, UVA-II: 320-340 nm) or UVB rays (280-320 nm). UV rays can cause acute and chronic damage to the skin, the type of damage depending on the wavelength of the radiation. For instance, UVB radiation can cause sunburn (erythema) extending to most severe burning of the skin. Other harmful effects of UVB rays include reduction in enzyme activities, weakening of the immune system, disturbances of the DNA structure and changes in the cell membrane. UVA rays penetrate into deeper layers of the skin where they can accelerate the aging process of the skin. The shorter wave UVA-II radiation additionally contributes to the development of sunburn. Moreover, UVA radiation can trigger phototoxic or photo allergic skin reactions. Frequent and unprotected irradiation of the skin by sunlight leads to a loss of skin elasticity and to increased development of wrinkles and in extreme cases, pathogenic changes in the skin extending to skin cancer are observed. To attenuate these negative effects of UV radiation, materials which absorb or reflect UV light, generally called UV absorbers, are used in cosmetic, dermatological and pharmacological preparations. The UV absorbers are classified as UVA and UVB absorbers depending on the location of their absorption maxima; if a UV absorber absorbs both UVA and UVB, it is referred to as a UVA/B broadband absorber.

The degree of efficacy of cosmetic, dermatological and pharmacological preparations for protection of the human skin from the erythema which is induced by UV radiation is determined by their Sun Protection Factor (SPF), which is the ratio of the energy required to show the first defined redness (erythema) of human skin which has been protected to the energy required to show the first defined redness of human skin which has not been protected. The amount of energy required to the first signs of erythema on human skin of Fitzpatrick classification 2 (light Caucasian) is 200 J/m2 which is also known as the Minimal Erythemal Dose (MED). Natural sunlight at 40° N on a clear day will deliver this dose in about 10 minutes. So a cosmetic, dermatological or pharmaceutical preparation for the protection of the human skin from the erythema with an SPF of 50 will theoretically protect skin from burning for 500 minutes. In addition to the SPF most regulatory authorities also stipulate that the formulations designed to protect human skin from erythema should also have sufficient absorption in the UVA range of the spectrum.

In order to achieve the desired protection from UV radiation cosmetic, dermatological and pharmacological preparations contain a mixture of UV filters with varying concentrations and the choice of UV filters used is determined by the legislation within the country or economic area. For example UV filters which can be used for the protection of skin are regulated in the USA by the America FDA via their OTC monograph system and are regulated in the European Union by the Cosmetic Regulation. Regulations covering the use of UV filters exist in other countries and regions as well. These regulations not only stipulate the filters which can be used but also fix a maximum usage level for each UV filter.

The two most common UVA filters available on the market are Avobenzone sold by the company Symrise under the trade name of Neo Heliopan® 357 and Bemotrizinol sold by the company Symrise under the trade name of Neo Heliopan® BMT. Both of these UV filters are solids and they have melting points above 80° C. rendering them with a compromised solubility when used at the maximum allowed concentrations. Therefore sufficient cosmetically accepted solvents have to be used to ensure that they remain dissolved in a final formulation. Both of these solid UV filters are applied to the heated oil phase in the manufacture of the formulation and this incorporation of high melting point solids requires energy and time, resulting in significant additional cost to the manufacturing process.

The UV filters are generally sold as individual ingredients but there are some examples of mixtures of UV filters available in the market, such as:
  Ethylhexyl Methoxycinnamate, Bemotrizinol, Ethylhexyl Triazone and Diethylamino Hydroxy Hexyl Benzoate in a mixture of emulsifiers, esters and water (trade name Uvinul® Easy) with the disadvantage that the formulator of the final product has to include the other auxiliary ingredients which reduces the flexibility to use other emulsifiers or auxiliary ingredients.
  Bemotrizinol in a polymeric aqueous dispersion with surfactants (trade names Tinosorb® Aqua and Tinosorb® Aqua Lite) with the disadvantage that the formulator of the final product has to include the other auxiliary ingredients which reduces the flexibility to use other emulsifiers or auxiliary ingredients
  Additionally a mixture of Diethylamino Hydroxy Hexyl Benzoate dissolved in Ethylhexyl Methoxycinnamate (trade name Uvinul® A Plus B) is sold as a broad spectrum UVA/UVB filter mix with the disadvantage that Ethylhexyl Methoxycinnamate is not photostable when combined with the most commonly used UVA filter Avobenzone.

OBJECT OF THE INVENTION

Therefore, it has been the object of the present invention providing a blend of UVA and UVB filters which are liquid and transparent at ambient temperatures, exhibit an improved photostability, particularly with regard to Avobenzone, and do not show tendency to recrystallize even when stored over long time at low temperatures.

BRIEF DESCRIPTION OF THE INVENTION

A first object of the present invention refers to a liquid and transparent blend of UV filters, comprising, consisting or essentially consisting of
(a) at least one solid UVA filter dissolved in
(b) at least one liquid UVB filter wherein said blend exhibits a linear UV absorbance curve with a variance of +/−10% in the range of 290 to 360 nm as measured from a solution containing 10 mg/l of said mixture in ethanol, and said solid UVA filters are selected from the group consisting of Avobenzone, Bemotrizinol and mixtures thereof. Another object has been providing a specific blend with an absorbance curve that is relatively flat in the region 290 to 360 nm.

The present invention provides a liquid mixture comprising the solid UVA filters Avobenzone and Bemotrizinol dissolved in liquid UVB filters such as preferably Octocrylene, Homosalate and Octisalate and generates a transparent solution without the addition of other auxiliary ingredients and which can be incorporated into an emulsion at ambient temperature without the need to use heat. The mixture is stable without exhibiting any recrystallisation of the solid components, even at −20° C. for at least 6 months. In addition, the combination has been chosen so that it can comply with the maximum concentration limits set by the regulatory authorities where the UV filters are allowed to be used and in addition, so that it optimally photostabilizes Avobenzone.

The chosen ratio of the individual components also has the attribute that the absorbance curve of the resulting mixture is relatively flat from the region 290 nm to 360 nm, which is the absorbance curve of a 10 mg/l of the mixture in ethanol. The wavelengths of UV radiation within this range would be more or less equally absorbed by the mixture, similar to the protection offered by being in the shadow of sunlight or similar to a neutral density filter within this range.

It has also surprisingly found that when using the mixture in cosmetic, dermatological and pharmaceutical formulations, a higher sun protection factor is obtained than by applying the UV filters individually into the same formulation, i.e., the SPF is boosted above what one who is familiar with the state of the art of sun care formulation would expect.

Despite the mixture containing a high amount of Octocrylene which is relatively heavy and has a sticky feeling when applied to the skin, the described mixture has a surprisingly dry and light touch when applied to the skin.

As explained above, the preferred liquid UVB filters are selected from the group consisting of Octocrylene, Homosalate, Octisalate and mixtures thereof.

In a preferred embodiment of the present invention the blend comprises, consists or essentially consists of
(a1) Avobenzone,
(a2) Bemotrizinol,
(b1) Octocrylene,
(b2) Octisalate, and
(b3) Homosalate.

More preferably the blend comprises
(a1) about 9 to about 15 wt.-%, preferably about 10 to about 12 wt.-% Avobenzone,
(a2) about 12 to about 25 wt.-%, preferably about 15 to about 20 wt.-% Bemotrizinol,
(b1) about 20 to about 35 wt.-%, preferably about 25 to about 30 wt.-% Octocrylene,
(b2) about 9 to about 15 wt.-% Octisalate, preferably about 10 to about 12 wt.-% and
(b3) about 9 to about 15 wt.-%, preferably about 10 to about 12 wt.-% Homosalate on condition that the amounts add to 100 wt.-%.

Compositions

Another object of the present invention relates to a composition, particularly a cosmetic, dermatologic or pharmaceutical composition comprising the blends as defined above, preferably in amounts of from about 0.5 to about 40 wt.-%, preferably from about 1 to about 30 wt.-%, more preferably from about 5 to about 25 wt.-% and most preferably from about 10 to about 20 wt.-%—calculated on the total composition.

The composition may represent for example a cosmetic cream, lotion, spray, emulsion, ointment, gel or mouse and the like. Typical examples are suncare products and facial moisturisers which also protect the skin against UV radiation The preparations according to the invention may contain antidandruff agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, hair promotion agents, cooling agents, skin-cooling agents, warming agents, skin-warming agents, stabilizers, UV-absorbing agents, UV filters, detergents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Non-ionic and cationic surfactants can be also present in the composition. Suitable examples are mentioned along with the paragraph dealing with emulsifiers.

Typical examples for anionic and zwitterionic surfactants encompass: Almondamidopropylamine Oxide, Almondamidopropyl Betaine, Aminopropyl Laurylglutamine, Ammonium C12-15 Alkyl Sulfate, Ammonium C12-16 Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium C12-15 Pareth Sulfate, Ammonium C9-10 Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Ammonium Myristyl Sulfate, Ammonium Nonoxynol-4 Sulfate, Ammonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AMPD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimoniumhydroxypropyl Butylglucosides Chloride, Butyldimoniumhydroxypropyl Laurylglucosides Chloride, Butyl Glucoside, Butylglucoside Caprate, Butylglucosides Hydroxypropyltrimonium Chloride, Butyloctanoic Acid, C18-36 Acid, C20-40 Acid, C30-50 Acid, C16-22 Acid Amide MEA, Calcium Dodecylbenzenesulfonate, Calcium Lauroyl Taurate, C9-16 Alkane/Cycloalkane, C10-14 Alkyl Benzenesulfonic Acid, C12-14 Alkyl Diaminoethylglycine HCL, C9-15 Alkyl Phosphate, *Candida bombicola*/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Capryloyl Collagen Amino Acids, Capryloyl Glycine, Capryloyl Hydrolyzed Collagen, Capryloyl Hydrolyzed Keratin, Capryloyl Keratin Amino Acids, Capryloyl Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, *Chrysanthemum sinense* Flower Extract, C12-14 Hydroxyalkyl Hydroxyethyl Beta-Alanine, C12-14 Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, C10-16 Pareth-1, C10-16 Pareth-2, C11-13 Pareth-6, C11-13 Pareth-9, C11-13 Pareth-10, C11-15 Pareth-30, C11-15 Pareth-40, C12-13 Pareth-1, C12-13 Pareth-23, C12-14 Pareth-5, C12-14 Pareth-9, C13-15 Pareth-21, C14-15 Pareth-8, C20-22 Pareth-30, C20-40 Pareth-40, C20-40 Pareth-95, C22-24 Pareth-33, C30-50 Pareth-40, C9-11 Pareth-6 Carboxylic Acid, C9-11 Pareth-8 Carboxylic Acid, C11-15 Pareth-7 Carboxylic Acid, C12-13 Pareth-5 Carboxylic Acid, C12-13 Pareth-7 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, C6-10 Pareth-4 Phosphate, C12-13 Pareth-2 Phosphate, C12-13 Pareth-10 Phosphate, C12-15 Pareth-6 Phosphate, C12-15 Pareth-8 Phosphate, C12-15 Pareth-10 Phosphate, C12-16 Pareth-6 Phosphate, C4-18 Perfluoroalkylethyl Thiohydroxypropyltrimonium Chloride, Cupuassuamidopropyl Betaine, DEA-C12-13 Alkyl Sulfate, DEA-C12-15 Alkyl Sulfate, DEA-Ceteareth-2 Phosphate, DEA-Cetyl Sulfate, DEA-Cocoamphodipropionate, DEA-C12-13 Pareth-3 Sulfate, DEA-Cyclocarboxypropyloleate, DEA-Dodecylbenzenesulfonate, DEA-Isostearate, DEA-Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-10 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-C1 2-15 Pareth-2 Phosphate, Di-C1 2-15 Pareth-4 Phosphate, Di-C1 2-15 Pareth-6 Phosphate, Di-C12-15 Pareth-8 Phosphate, Di-C1 2-15 Pareth-10 Phosphate, Didodecyl Butanetetracarboxylate, Diethylamine Laureth Sulfate, Diethylhexyl Sodium Sulfosuccinate, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dilaureth-4 Phospate, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DIPA-Lanolate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Caproamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropylsulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium C12-14 Pareth-1 Sulfosuccinate, Disodium C12-14 Pareth-2 Sulfosuccinate, Disodium C12-15 Pareth Sulfosuccinate, Disodium C12-14 Sec-Pareth-3 Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphodiacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-Isodeceth-7 Carboxyamphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinamate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamphodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecyl benzene Sulfonic Acid, Erucamidopropyl Hydroxysultaine, Ethylhexeth-3 Carboxylic Acid, Ethyl PEG-15 Cocamine Sulfate, Glyceryl Capryl EtherHexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed *Candida bombicola* Extract, Hydroxyceteth-60, Hydroxyethyl Acetomonium PG-Dimethicone, Hydroxyethylbutylamine Laureth Sulfate, Hydroxyethyl Carboxymethyl Cocamidopropylamine, Hydroxyethyl Hydroxypropyl C12-15 Alkoxypropylamine Oxide, Hydroxylauryl/Hydroxymyristyl Betaine, Hydroxystearic Acid, Hydroxysuccinimidyl C10-40 lsoalkyl Acidate, Hydroxysuccinimidyl C21-22 Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, Isoceteth-30, Isolaureth-4 Phosphate, Isopolyglyceryl-3 Dimethicone, Isopolyglyceryl-3 Dimethiconol, Isopropanolamine Lanolate, Isopropylamine Dodecylbenzenesulfonate, Isostearamidopropylamine Oxide, Isostearamidopropyl Betaine, Isostearamidopropyl Morpholine Oxide, Isosteareth-8, Isosteareth-16, Isosteareth-22, Isosteareth-25, Isosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylglucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Laurie Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspolymer, Lauryldimoniumhydroxypropyl Cocoglucosides Chloride, Lauryl Glucoside, Laurylglucosides Hydroxypropyltrimonium Chloride, Lauryl Glycol Hydroxypropyl Ether, Lauryl Hydroxysultaine, Lauryl Malamide, Lauryl Methylglucamide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, Macadamia Seed Oil Glycereth-8 Esters, Magnesium Coceth Sulfate, Magnesium Coco-Sulfate, Magnesium Isododecylbenzenesulfonate, Magnesium Laureth-11 Carboxylate, Magnesium Laureth Sulfate, Magnesium Laureth-5 Sulfate, Magnesium Laureth-8 Sulfate, Magnesium Laureth-16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Steareth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amido Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA C12-15

Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkonium Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myristaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate, Ozonized PEG-14 Oleate, Ozonized Polysorbate 80, Palm Acid, Palmamidopropyl Betaine, Palmeth-2 Phosphate, Palmitamidopropylamine Oxide, Palmitamidopropyl Betaine, Palmitamine Oxide, Palmitic Acid, Palmitoyl Collagen Amino Acids, Palmitoyl Glycine, Palmitoyl Hydrolyzed Collagen, Palmitoyl Hydrolyzed Milk Protein, Palmitoyl Hydrolyzed Wheat Protein, Palmitoyl Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide, PEG-6 Cocamide Phosphate, PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120 Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40 Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50

Tallow Amide, PEG-2 Tallowamide DEA, PEG-20 Tallowate, PEG-66 Trihydroxystearin, PEG-200 Trihydroxystearin, PEG-60 Tsubakiate Glycerides, Pelargonic Acid, Pentadoxynol-200, Pheneth-6 Phosphate, Poloxamer 105, Poloxamer 108, Poloxamer 182, Poloxamer 183, Poloxamer 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, Pomaderris Kumerahou Flower/Leaf Extract, *Poria cocos* Extract, Potassium Abietoyl Hydrolyzed Collagen, Potassium Babassuate, Potassium Behenate, Potassium C9-15 Alkyl Phosphate, Potassium C11-15 Alkyl Phosphate, Potassium C12-13 Alkyl Phosphate, Potassium C12-14 Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium Isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Olivoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Coco/Isostearamide, PPG-2-Isodeceth-8, PPG-2-Isodeceth-10, PPG-2-Isodeceth-18, PPG-2-Isodeceth-25, PPG-4-Isodeceth-10, Propyltrimonium Hydrolyzed Collagen, Quaternium-24, Quaternium-52, Quaternium-87, Rapeseed Acid, Rice Bran Acid, Rice Oil Glycereth-8 Esters, Ricinoleamidopropyl Betaine, Ricinoleic Acid, Ricinoleth-40, Safflower Acid, Sapindus Oahuensis Fruit Extract, *Saponaria officinalis* Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium Astrocaryum Murumuruate, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate Lauryl-Glucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium C13-17 Alkane Sulfonate, Sodium C14-18 Alkane Sulfonate, Sodium C12-15 Alkoxypropyl Iminodipropionate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium C9-22 Alkyl Sec Sulfonate, Sodium C14-17 Alkyl Sec Sulfonate, Sodium Caprate, Sodium Caproamphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoa m phoacetate, Sodium Cocoa m phohydroxypropylsulfonate, Sodium Cocoamphopropionate, Sodium Cocoate, Sodium Coco/Babassu/Andiroba Sulfate, Sodium Coco/Babassu Sulfate, Sodium Cocoglucosides Hydroxypropyl Phosphate, Sodium Cocoglucosides Hydroxypropylsulfonate, Sodium Coco-Glucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium Coco-Sulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium C12-14 Olefin Sulfonate, Sodium C14-16 Olefin Sulfonate, Sodium C14-18 Olefin Sulfonate, Sodium C16-18 Olefin Sulfonate, Sodium Cornamphopropionate, Sodium Cottonseedamphoacetate, Sodium C13-15 Pareth-8 Butyl Phosphate, Sodium C9-11 Pareth-6 Carboxylate, Sodium C11-15 Pareth-7 Carboxylate, Sodium C12-13 Pareth-5 Carboxylate, Sodium C12-13 Pareth-8 Carboxylate, Sodium C12-13 Pareth-12 Carboxylate, Sodium C12-15 Pareth-6 Carboxylate, Sodium C12-15 Pareth-7 Carboxylate, Sodium C12-15 Pareth-8 Carboxylate, Sodium C14-15 Pareth-8 Carboxylate, Sodium C12-14 Sec-Pareth-8 Carboxylate, Sodium C14-15 Pareth-PG Sulfonate, Sodium C12-13 Pareth-2 Phosphate, Sodium C13-15 Pareth-8 Phosphate, Sodium C9-15 Pareth-3 Sulfate, Sodium C10-15 Pareth Sulfate, Sodium C10-16 Pareth-2 Sulfate, Sodium C12-13 Pareth Sulfate, Sodium C12-15 Pareth Sulfate, Sodium C12-15 Pareth-3 Sulfate, Sodium C13-15 Pareth-3 Sulfate, Sodium C12-14 Sec-Pareth-3 Sulfate, Sodium C12-15 Pareth-3 Sulfonate, Sodium C12-15 Pareth-7 Sulfonate, Sodium C12-15 Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decylglucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylbenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer, Sodium Hydroxystearate, Sodium Isostearate, Sodium Isostearate-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Lauriminodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl Glycine Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopalmitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl Isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoamphohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium *Passiflora edulis* Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Saffloweroyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl Glycine, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen, Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium *Theobroma grandiflorum* Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine, Stearyldimoniumhydroxypropyl Butylglucosides Chloride, Stearyldimoniumhydroxypropyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine, Tallow Dihydroxyethyl Betaine, Tallowoyl Ethyl Glucoside, TEA-Abietoyl Hydrolyzed Collagen, TEA-C12-14 Alkyl Phosphate, TEA-C10-15 Alkyl Sulfate, TEA-C11-15 Alkyl Sulfate, TEA-C12-13 Alkyl Sulfate, TEA-C12-14 Alkyl Sulfate, TEA-C12-15 Alkyl Sulfate, TEA C14-17 Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA-Dimethicone PEG-7 Phosphate, TEA-Dodecylbenzenesulfonate, TEA-Hydrogenated Cocoate, TEA-Hydrogenated Tallowoyl Glutamate, TEA-Isostearate, TEA-Isostearoyl Hydrolyzed Collagen, TEA-Lauraminopropionate, TEA-Laurate, TEA-Laurate/Myristate, TEA-Laureth Sulfate, TEA-Lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate, TEA-Rosinate, TEA-Stearate, TEA-Tallate, TEA-T ridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TIPA-Lauryl Sulfate, TIPA-Myristate, TIPA-Stearate, Tocopheryl Phosphate, Trehalose Undecylenoate, TM-C12-15 Pareth-2 Phosphate, TM-C12-15 Pareth-6 Phosphate, TM-C12-15 Pareth-8 Phosphate, TM-C12-15 Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylen-amidopropylamine Oxide, Undecylenamidopropyl Betaine, Undecylenic Acid, Undecylenoyl Collagen Amino Acids, Undecylenoyl Glycine, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, *Yucca schidigera* Leaf/Root/Stem Extract, *Yucca schidigera* Stem Extract, Zinc Coceth Sulfatea and Zinc Coco-Sulfate.

Preferred are one or more compounds selected from the group consisting of Sodium Laureth Sulfate, Cocamidopropyl Betaine, Sodium Cocoamphoacetate, CocoGlucoside and Ammonium Lauryl Sulfosuccinate.

The percentage content of surfactants in the preparations may be from 0.1 to 10% by weight and is preferably from 0.5 to 5% by weight, based on the preparation.

Oil Bodies

The composition may also contain oil bodies, also called lipids, such as for example:
(i) linear or branched saturated paraffins (mineral oils) having 15 or more C atoms, in particular having 18 to 45 C atoms;
(ii) esters having 12 or more C atoms of linear or branched fatty acids having 6 to 30 C atoms and linear or branched, saturated or unsaturated mono-, di- or triols having 3 to 30 C atoms, these esters having no free hydroxyl groups;

(iii) esters of benzoic acid and linear or branched, saturated or unsaturated monoalkanols having 8 to 20 C atoms;
(iv) monoesters or diesters of alcohols having 3 to 30 C atoms and naphthalenemonocarboxylic or -dicarboxylic acids; especially naphthalenemonocarboxylic acid $C_6$-$C_{18}$ esters and naphthalenedicarboxylic acid di-$C_6$-$C_{18}$ esters;
(v) linear or branched, saturated or unsaturated di-$C_6$-$C_{18}$-alkyl ethers;
(vi) silicone oils;
(vii) 2-alkyl-1-alkanols of the formula (III)

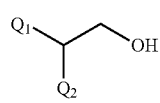

(III)

where
$Q_1$ is a linear or branched alkyl radical having 6 to 24 C atoms and
$Q_2$ is a linear or branched alkyl radical having 4 to 16 C atoms.

An oil phase or oil component in the narrower (and preferred) sense of the present invention, i.e. of the inventively limited substances or substances present only in a minor fraction, encompasses the following groups of substances:
(i) linear or branched, saturated paraffins having 20 to 32 C atoms;
(ii) esters having at least 14 C atoms of linear or branched, saturated fatty acids having 8 to 24 C atoms and linear or branched, saturated or unsaturated mono-, di- or triols having 3 to 24 C atoms, these esters containing no free hydroxyl groups;
(iii) esters of benzoic acid and linear or branched, saturated monoalkanols having 10 to 18 C atoms;
(iv) Alkylenediol dicaprylate caprates especially propylenediol dicaprylate caprate;
(v) linear or branched, saturated di-C6-C18-alkyl ethers, especially (straight-chain) di-C6-C12-alkyl ethers;
(vi) silicone oils from the group of the cyclotrisiloxanes, cyclopentasiloxanes, dimethylpolysiloxanes, diethylpolysiloxanes, methylphenylpolysiloxanes, diphenylpolysiloxanes and hybrid forms thereof;
(vii) 2-alkyl-1-alkanols having 12 to 32 C atoms of the formula (III) where $Q_1$ is a (preferably linear) alkyl radical having 6 to 18 C atoms and $Q_2$ is a (preferably linear) alkyl radical having 4 to 16 C atoms.

An oil phase in the narrowest (and most preferred) sense of the present invention encompasses the following groups of substances:
(i) linear or branched, saturated paraffins having 20 to 32 C atoms such as isoeicosane or squalane;
(ii) esters having at least 16 C atoms of linear or branched, saturated fatty acids having 8 to 18 C atoms and linear or branched, saturated mono-, di- or triols having 3 to 18 C atoms, these esters containing no free hydroxyl groups;
(iii) esters of benzoic acid and linear or branched, saturated monoalkanols having 12 to 15 C atoms, especially C12-15-alkyl benzoates;
(iv) Alkylenediol dicaprylate caprates especially propylenediol dicapylate caprate;
(v) straight-chain di-$C_6$-$C_{10}$-alkyl ethers; especially di-n-octyl ether (dicaprylyl ether);
(vi) silicone oils from the group undecamethylcyclotrisiloxane, cyclomethicone, decamethylcyclopentasiloxane, dimethylpolysiloxanes, diethylpolysiloxanes, methylphenylpolysiloxanes and diphenylpolysiloxanes;
(vii) 2-alkyl-1-alkanols having 12 to 32 C atoms of the formula (III) where $Q_1$ is a (preferably linear) alkyl radical having 6 to 18 C atoms and $Q_2$ is a (preferably linear) alkyl radical having 4 to 16 C atoms.

Particularly preferred components of type (i) in the oil phase are as follows: isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, caprylic/capric triglyceride, Alkylenediol dicaprylate caprates especially propylenediol dicapylate caprate; and also synthetic, semisynthetic and natural mixtures of such esters, e.g. jojoba oil.

Fatty acid triglycerides (oil components of type (i) in the oil phase) may also be in the form of, or in the form of a constituent of, synthetic, semisynthetic and/or natural oils, examples being olive oil, sunflower oil, soya oil, peanut oil, rapeseed oil, almond oil, palm oil, coconut oil, palm kernel oil and mixtures thereof.

Particularly preferred oil components of type (vii) in the oil phase are as follows: 2-butyl-1-octanol, 2-hexyl-1-decanol, 2-octyl-1-dodecanol, 2-decyltetradecanol, 2-dodecyl-1-hexadecanol and 2-tetradecyl-1-octadecanol.

Particularly preferred oil components in the oil phase are mixtures comprising $C_{12}$-$C_{15}$-alkyl benzoate and 2-ethylhexyl isostearate, mixtures comprising $C_{12}$-$C_{15}$-alkyl benzoate and isotridecyl isononanoate, mixtures comprising $C_{12}$-$C_{15}$-alkyl benzoate, 2-ethylhexyl isostearate and isotridecyl isononanoate, mixtures comprising cyclomethicone and isotridecyl isononanoate, and mixtures comprising cyclomethicone and 2-ethylhexyl isostearate.

Preferred oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other non-ionic or cationic surfactants may also be added to the preparations as emulsifiers, including for example:
- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera BeMina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)$ $X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine-based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

The use of a combination of anionic and/or amphoteric surfactants with one or more nonionic surfactants is further advantageous. In a preferred embodiment according to the invention the composition further comprises emulsifiers selected from the group consisting of:
  Alkyl phosphate derivatives
  Glyceryl oleate citrate derivatives
  Glyceryl stearate citrate derivatives
  Stearic acid esters
  Sorbitan esters
  Ethoxylated sorbitan esters
  Ethoxylated mono-, di- and tri glycerides
  Methyl glucose esters Superfatting Agents and Consistency Factors Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. THICKENING AGENTS AND RHEOLOGY ADDITIVES Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable polymers to improve the spreadability of the composition upon the skin or hair, or improve the water and or sweat and or rub-off resistancy of the formula and to improve the protection factor of the composition. Examples of such polymers are: VP/Eicosene copolymers sold under the trade name of Antaron V-220 by International Speciality Products, VP/Hexadecene copolymer sold under the trade names Antaron V-216 and Antaron V-516 by International Speciality Products, Tricontanyl PVP sold under the trade name of Antaron WP-660 by International Speciality Products, Isohexadecane and Ethylene/Propylene/Styrene copolymer and Butylene/Styrene copolymer sold under the trade names of Versagel MC and MD by Penreco, Hydrogenated polyisobutene and Ethylene/Propylene/Styrene copolymer and Butylene/Styrene copolymer sold under the trade mane of Versagel ME by Penreco, Acrylates/Octylacrylamide Copolymers sold under the trade name of Dermacryl 79, Dermacryl AQF and Dermacryl LT by AkzoNobel, Polyurethanes such as PPG-17/IPDI/DMPA copolymer sold under the trade name of Avalure UR 450 & 525 sold by Noveon, Polyurethanes-2 and -4 sold under the trade names Avalure UR-405, -410, -425, -430 and -445 525 sold by Noveon, Polyurethane 5 and Butyl Acetate and isopropyl alcohol sold under the trade name Avalure UR-510 and -525 sold by Noveon, Polyurethanes-1 and -6 sold under the trade name of Luviset PUR by BASF, Hydrogenated Dimer Dilinoleyl/Dimethylcarbonate Copolymer sold under the trade name of Cosmedia DC by Cognis.

Of course, as one well versed in the art of cosmetic, dermatological and pharmacological compositions knows, this is not an exhaustive list and other suitable polymers not listed here may be used. Examples of such polymers may be found in the latest edition of the CTFA's International Cosmetic Ingredient Dictionary The amount of polymers used to obtain the desired effect in the formulation range from 0.10% to 5.0% by weight of the composition and especially in the range from 0.25% to 3.0% by weight of the composition.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicones can be chosen from the group consisting of: Acefylline Methylsilanol Mannuronate, Acetylmethionyl Methylsilanol Elastinate Acrylates/Behenyl, Acrylate/Dimethicone Methacrylate Copolymer, Acrylates/Behenyl Methacrylate/Dimethicone Methacrylate Copolymer, Acrylates/Bis-Hydroxypropyl Dimethicone Crosspolymer, Acrylates/Dimethicone Copolymer, Acrylates/Dimethicone Methacrylate/Ethylhexyl Acrylate Copolymer, Acrylates/Dimethiconol Acrylate Copolymer, Acrylates/Ethylhexyl Acrylate/Dimethicone Methacrylate Copolymer, Acrylates/Octyl-acrylamide/Diphenyl Amodimethicone Copolymer, Acrylates/Polytri-methylsiloxymethacrylate Copolymer, Acrylates/Propyl Trimethicone Methacrylate Copolymer, Acrylates/Stearyl Acrylate/Dimethicone Methacrylate Copolymer, Acrylates/Tridecyl Acrylate/Triethoxysilylpropyl Methacrylate/Dimethicone Methacrylate Copolymer, Acrylates/Trifluoropropylmethacrylate/Polytrimethyl Siloxymethacrylate Copolymer, Amino Bispropyl Dimethicone, Aminoethylaminopropyl Dimethicone, Aminopropyl Dimethicone, Aminopropyl Phenyl Trimethicone, Aminopropyl Triethoxysilane, Ammonium Dimethicone PEG-7 Sulfate, Amodimethicone, Amodimethicone Hydroxystearate, Amodimethicone/Silsesquioxane Copolymer, Ascorbyl Carboxydecyl Trisiloxane, Ascorbyl Methylsilanol Pectinate, Behenoxy Dimethicone, Behentrimonium Dimethicone PEG-8 Phthalate, Behenyl Dimethicone, Bisamino PEG/PPG-41/3 Aminoethyl PG-Propyl Dimethicone, Bis-Aminopropyl/Ethoxy Aminopropyl Dimethicone, Bis(Butylbenzoate) Diaminotriazine Aminopropyltrisiloxane, Bis-Butyldimethicone Polyglyceryl-3, Bis-Butyloxyamodimethicone/PEG-60 Copolymer, Bis (C13-15 Alkoxy) Hydroxybutamidoamodimethicone, Bis (C13-15 Alkoxy) PG-Amodimethicone, Bis-(C1-8 Alkyl Lauroyl Lysine Decylcarboxamide) Dimethicone, Bis-Cetyl Cetyl Dimethicone, Bis-Cetyl/PEG-8 Cetyl PEG-8 Dimethicone, Bis-Diphenylethyl Disiloxane, Bis-Ethyl Ethyl Methicone, Bis-Gluconamidoethylaminopropyl Dimethicone, Bis-Hydrogen Dimethicone, Bis-Hydroxyethoxypropyl Dimethicone Bis-Hydroxylauryl, Dimethicone/IPDI Copolymer, Bis-Hydroxy/Methoxy Amodimethicone, Bis-Hydroxypropyl Dimethicone Behenate, Bis-Hydroxypropyl Dimethicone/SMDI Copolymer, Bis-Isobutyl PEG-14/Amodimethicone Copolymer, Bis-Isobutyl PEG-15/Amodimethicone Copolymer, Bis-Isobutyl PEG/PPG-20/35/Amodimethicone Copolymer, Bis-Isobutyl PEG/PPG-10/7/Dimethicone Copolymer, Bis-Isobutyl PEG-24/PPG-7/Dimethicone Copolymer, Bis-PEG-1 Dimethicone, Bis-PEG-4 Dimethicone, Bis-PEG-8 Dimethicone, Bis-PEG-12 Dimethicone, Bis-PEG-20 Dimethicone, Bis-PEG-12 Dimethicone Beeswax, Bis-PEG-12 Dimethicone Candelillate, Bis-PEG-15 Dimethicone/IPDI Copolymer, Bis-PEG-15 Methyl Ether Dimethicone, Bis-PEG-18 Methyl Ether Dimethyl Silane, Bis-PEG/PPG-14/14 Dimethicone, Bis-PEG/PPG-15/5 Dimethicone, Bis-PEG/PPG-18/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Bisphenylhexamethicone, Bis-Phenylpropyl Dimethicone, Bispolyethylene Dimethicone, Bis-(Polyglyceryl-3 Oxyphenylpropyl) Dimethicone, Bis-(Polyglyceryl-7 Oxyphenylpropyl) Dimethicone, Bis-PPG-15 Dimethicone/IPDI Copolymer, Bis(PPG-7 Undeceneth-21) Dimethicone, Bis-Stearyl Dimethicone, Bis-Trimethoxysilylethyl Tetramethyldisiloxyethyl Dimethicone, Bis-Vinyldimethicone, Bis-Vinyl Dimethicone/Dimethicone Copolymer, Borage Seed Oil PEG-7 Dimethicone Esters, Butyl Acrylate/C6-14 Perfluoroalkylethyl Acrylate/Mercaptopropyl Dimethicone Copolymer, Butyl Acrylate/Hydroxypropyl Dimethicone Acrylate Copolymer, Butyl Dimethicone Acrylate/Cyclohexylmethacrylate/Ethylhexyl Acrylate Copolymer, Butyldimethicone Methacrylate/Methyl Methacrylate Crosspolymer, t-Butyl Dimethyl Silyl Grape Seed Extract, Butyl Polydimethylsiloxyl Ethylene/Propylene/Vinylnorbornene Copolymer, C6-8 Alkyl C3-6 Alkyl Glucoside Dimethicone, C20-24 Alkyl Dimethicone, C24-28 Alkyl Dimethicone, C26-28 Alkyl Dimethicone, C30-45 Alkyl Dimethicone, C30-60 Alkyl Dimethicone, C32 Alkyl Dimethicone, C30-45 Alkyl Dimethicone/Polycyclohexene Oxide Crosspolymer, C26-28 Alkyldimethylsilyl Polypropylsilsesquioxane, C30-45 Alkyldimethylsilyl Polypropylsilsesquioxane, C20-24 Alkyl Methicone, C24-28 Alkyl Methicone, C26-28 Alkyl Methicone, C30-45 Alkyl Methicone, C20-28 Alkyl Perfluorodecylethoxy Dimethicone, C26-54 Alkyl Tetradecyl Dimethicone, Capryl Dimethicone, Caprylyl Dimethicone Ethoxy Glucoside, Caprylyl Methicone, Caprylyl Trimethicone, Carboxydecyl Trisiloxane, Castor Oil Bis-Hydroxypropyl Dimethicone Esters Cerotyl Dimethicone, Cetearyl Dimethicone Crosspolymer, Cetearyl Dimethicone/Vinyl Dimethicone Crosspolymer, Cetearyl Methicone, Cetrimonium Carboxydecyl PEG-8 Dimethicone, Cetrimonium Dimethicone PEG-7 Phthalate, Cetyl Behenyl Dimethicone, Cetyl Dimethicone, Cetyl Dimethicone/Bis-Vinyldimethicone Crosspolymer, Cetyl Hexacosyl Dimethicone, Cetyloxy Dimethicone, Cetyl PEG-8 Dimethicone, Cetyl PEG/PPG-15/15 Butyl Ether Dimethicone, Cetyl PEG/PPG-7/3 Dimethicone, Cetyl PEG/PPG-10/1 Dimethicone, Cetyl Triethylmonium Dimethicone PEG-8 Phthalate, Cetyl Triethylmonium Dimethicone PEG-8 Succinate, Copper Acetyl Tyrosinate Methylsilanol, Copper PCA Methylsilanol, C4-14 Perfluoroalkylethoxy Dimethicone, Cycloethoxymethicone, Cycloheptasiloxane, Cyclohexasiloxane, Cyclomethicone, Cyclopentasiloxane, Cyclophenylmethicone, Cyclotetrasiloxane, mCyclovinylmethicone, Cystine Bis-PG-Propyl Silanetriol, DEA PG-Propyl PEG/PPG-18/21 Dimethicone, Diisostearoyl Trimethylolpropane Siloxy Silicate, Dilauroyl Trimethylolpropane Siloxy Silicate, Dilinoleamidopropyl Dimethylamine Dimethicone PEG-7 Phosphate, Dimethicone, Dimethicone Crosspolymer, Dimethicone Crosspolymer-3, Dimethicone/Divinyldimethicone/Silsesquioxane Crosspolymer, Dimethicone Ethoxy Glucoside, Dimethicone Hydroxypropyl Trimonium Chloride, Dimethicone/Mercaptopropyl Methicone Copolymer, Dimethicone PEG-15 Acetate Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone/PEG-10 Crosspolymer, Dimethicone/PEG-10/15 Crosspolymer, Dimethicone/PEG-15 Crosspolymer, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phosphate, Dimethicone PEG-8 Phosphate, Dimethicone PEG-10 Phosphate, Dimethicone PEG-7 Phthalate, Dimethicone PEG-8 Phthalate, Dimethicone PEG-8 Polyacrylate, Dimethicone PEG/PPG-20/23 Benzoate, Dimethicone PEG/PPG-7/4 Phosphate, Dimethicone PEG/PPG-12/4 Phosphate, Dimethicone PEG-7 Succinate, Dimethicone PEG-8 Succinate, Dimethicone PEG-7 Sulfate, Dimethicone PEG-7 Undecylenate, Dimethicone PG-Diethylmonium Chloride, Dimethicone/Phenyl Vinyl Dimethicone Crosspolymer, Dimethicone/Polyglycerin-3 Crosspolymer, Dimethicone/PPG-20 Crosspolymer, Dimethicone Propylethylenediamine Behenate, Dimethicone Propyl PG-Betaine, Dimethicone/Silsesquioxane Copolymer, Dimethicone Silylate, Dimethicone?/inyl Dimethicone Crosspolymer, Dimethicone/Vinyltrimethylsiloxysilicate Crosspolymer, Dimethiconol, Dimethiconol Arginine, Dimethiconol Beeswax, Dimethiconol Behenate, Dimethiconol Borageate, Dimethiconol Candelillate, Dimethiconol Carnaubate, Dimethiconol Cysteine, Dimethiconol Dhupa Butterate, Dimethiconol Fluoroalcohol Dilinoleic Acid, Dimethiconol Hydroxystearate, Dimethiconol Illipe Butterate, Dimethiconol/IPDI Copolymer, Dimethiconol Isostearate, Dimethiconol Kokum Butterate, Dimethiconol Lactate, Dimethiconol Meadowfoamate, Dimethiconol Methionine, Dimethiconol/Methylsilanol/Silicate Crosspolymer, Dimethiconol Mohwa Butterate, Dimethiconol Panthenol, Dimethiconol Sal Butterate, Dimethiconol/Silica Crosspolymer, Dimethiconol/Silsesquioxane Copolymer, Dimethiconol Stearate, Dimethiconol/Stearyl, Methicone/Phenyl Trimethicone Copolymer, Dimethoxysilyl Ethylenediaminopropyl Dimethicone, Dimethylaminopropylamido PCA Dimethicone, Dimethyl Oxobenzo Dioxasilane, Dimethylsilanol Hyaluronate, Dioleyl Tocopheryl Methylsilanol, Diphenyl Amodimethicone, Diphenyl Dimethicone, Diphenyl Dimethicone Crosspolymer Diphenyl Dimethicone?/inyl Diphenyl Dimethicone/Silsesquioxane Crosspolymer, Diphenylethyl Benzyloxy Dilsiloxane, Diphenylisopropyl Dimethicone, Diphenylsiloxy Phenyl/Propyl Trimethicone, Diphenylsiloxy Phenyl Trimethicone Disiloxane, Disodium Amodimethicone Disuccinamide, Disodium PEG-12 Dimethicone Sulfosuccinate, Disodium PEG-8 Lauryl Dimethicone Sulfosuccinate, Divinyldimethicone/Dimethicone Copolymer, Divinyldimethicone/Dimethicone Crosspolymer, Drometrizole Trisiloxane, Ethylhexyl Acrylate/VP/Dimethicone Methacrylate Copolymer, Ethyl Methicone, Ethyl Trisiloxane, Fluoro C2-8 Alkyldimethicone, Gluconamidopropyl Aminopropyl Dimethicone, 4-(2-Beta-Glucopyranosiloxy) Propoxy-2-Hydroxybenzophenone, Glyceryl Undecyl Dimethicone, Glycidoxy Dimethicone, Hexadecyl Methicone, Hexyl Dimethicone, Hexyl Methicone, Hexyltrimethoxysilane, Hydrogen Dimethicone, Hydrogen Dimethicone/Octyl Silsesquioxane Copolymer, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protein PG-Propyl Methylsilanediol, Hydrolyzed Wheat Protein PG-Propyl Silanetriol, Hydroxyethyl Acetomonium PG-Dimethicone, Hydroxypropyldimethicone, Hydroxypropyl Dimethicone Behenate, Hydroxypropyl Dimethicone Isostearate, Hydroxypropyl Dimethicone Stearate, Isobutylmethacrylate/Bis-Hydroxypropyl Dimethicone Acrylate Copolymer, Isobutylmethacrylate/Trifluoroethylmethacrylate/Bis-Hydroxypropyl Dimethicone Acrylate Copolymer, Isopentyl Trimethoxycinnamate Trisiloxane, Isopolyglyceryl-3 Dimethicone, Isopolyglyceryl-3 Dimethiconol, Isopropyl Titanium Triisostearate/Triethoxysilylethyl, Polydimethylsiloxyethyl Dimethicone Crosspolymer, Isostearyl Carboxydecyl PEG-8 Dimethicone, Lactoyl Methylsilanol Elastinate, Lauryl Dimethicone, Lauryl Dimethicone PEG-15 Crosspolymer, Lauryl Dimethicone PEG-10 Phosphate, Lauryl Dimethicone/Polyglycerin-3 Crosspolymer, Lauryl Methicone, Lauryl PEG-8 Dimethicone, Lauryl PEG-10 Methyl Ether Dimethicone, Lauryl PEG-9 Polydimethylsiloxyethyl Dimethicone, Lauryl PEG/PPG-18/18 Methicone, Lauryl Phenylisopropyl Methicone, Lauryl Phenylpropyl Methicone, Lauryl Polydimethylsiloxyethyl Dimethicone/Bis-Vinyldimethicone Crosspolymer, Lauryl Polyglyceryl-3 Polydimethylsiloxyethyl Dimethicone, Lauryl Trimethicone, Linoleamidopropyl PG-Dimonium Chloride Phosphate Dimethicone, Methacryloyl Propyltrimethoxysilane, Methicone, Methoxy Amodimethicone/Silsesquioxane Copolymer, Methoxycinnamidopropyl Polysilsesquioxane, Methoxycinnamoylpropyl Silsesquioxane Silicate, Methoxy PEG-13 Ethyl Polysilsesquioxane, Methoxy PEG/PPG-7/3 Aminopropyl Dimethicone, Methoxy PEG/PPG-25/4 Dimethicone, Methoxy PEG-10 Propyltrimethoxysilane, Methyleugenyl PEG-8 Dimethicone, Methylpolysiloxane Emulsion, Methylsilanol Acetylmethionate, Methylsilanol Acetyltyrosine, Methylsilanol Ascorbate, Methylsilanol Carboxymethyl Theophylline, Methylsilanol Carboxymethyl Theophylline Alginate, Methylsilanol Elastinate, Methylsilanol Glycyrrhizinate, Methylsilanol Hydroxyproline, Methylsilanol Hydroxyproline Aspartate, Methylsilanol Mannuronate, Methylsilanol PCA, Methylsilanol PEG-7 Glyceryl Cocoate, Methylsilanol/Silicate Crosspolymer, Methylsilanol Spirulinate, Methylsilanol Tri-PEG-8 Glyceryl Cocoate, Methyl Trimethicone, Methyltrimethoxysilane, Myristylamidopropyl Dimethylamine Dimethicone PEG-7 Phosphate, Myristyl Methicone, Myristyl Trisiloxane, Nylon-611/Dimethicone Copolymer, PCA Dimethicone, PEG-7 Amodimethicone, PEG-8 Amodimethicone, PEG-8 Cetyl Dimethicone, PEG-3 Dimethicone, PEG-6 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-10 Dimethicone Crosspolymer, PEG-12 Dimethicone Crosspolymer, PEG-8 Dimethicone Dimer Dilinoleate, PEG-8 Dimethicone/Dimer Dilinoleic Acid Copolymer, PEG-10 Dimethicone/Vinyl Dimethicone Crosspolymer, PEG-8 Distearmonium Chloride PG-Dimethicone, PEG-10/Lauryl Dimethicone Crosspolymer, PEG-15/Lauryl Dimethicone Crosspolymer, PEG-15/Lauryl Polydimethylsiloxyethyl Dimethicone Crosspolymer, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10

Methyl Ether Dimethicone, PEG-11 Methyl Ether Dimethicone, PEG-32 Methyl Ether Dimethicone, PEG-8 Methyl Ether Triethoxysilane, PEG-10 Nonafluorohexyl Dimethicone Copolymer, PEG-4 PEG-12 Dimethicone, PEG-8 PG-Coco-Glucoside Dimethicone, PEG-9 Polydimethylsiloxyethyl Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6 Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, PEG/PPG-30/10 Dimethicone, PEG/PPG-25/25 Dimethicone/Acrylates Copolymer, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG/PPG-5/3 Trisiloxane, PEG-4 Trifluoropropyl Dimethicone Copolymer, PEG-8 Trifluoropropyl Dimethicone Copolymer, PEG-10 Trifluoropropyl Dimethicone Copolymer, PEG-8 Trisiloxane, Perfluorocaprylyl riethoxysilylethyl Methicone, Perfluorononyl Dimethicone, Perfluorononyl Dimethicone/Methicone/Amodimethicone Crosspolymer, Perfluorononylethyl Carboxydecyl Behenyl Dimethicone, Perfluorononylethyl Carboxydecyl Hexacosyl Dimethicone, Perfluorononylethyl Carboxydecyl Lauryl/Behenyl Dimethicone, Perfluorononylethyl Carboxydecyl Lauryl Dimethicone, Perfluorononylethyl Carboxydecyl PEG-8 Dimethicone, Perfluorononylethyl Carboxydecyl PEG-10 Dimethicone, Perfluorononylethyl Dimethicone/Methicone Copolymer, Perfluorononylethyl PEG-8 Dimethicone, Perfluorononylethyl Stearyl Dimethicone, Perfluorooctylethyl/Diphenyl Dimethicone Copolymer, Perfluorooctylethyl Triethoxysilane, Perfluorooctylethyl Trimethoxysilane, Perfluorooctylethyl Trisiloxane, Perfluorooctyl Triethoxysilane, PG-Amodimethicone, Phenethyl Dimethicone, Phenethyl Disiloxane, Phenyl Dimethicone, Phenylisopropyl Dimethicone, Phenyl Methicone, Phenyl Methiconol, Phenylpropyldimethylsiloxysilicate, Phenylpropyl Ethyl Methicone, Phenyl Propyl Trimethicone, Phenyl Propyl Trimethicone/Diphenylmethicone, Phenyl Trimethicone, Platinum Divinyldisiloxane, Polyacrylate-6, Polydiethylsiloxane, Polydimethylsiloxyethyl Dimethicone/Bis-Vinyldimethicone Crosspolymer, Polydimethylsiloxyethyl Dimethicone/Methicone Copolymer, Polydimethylsiloxy PEG/PPG-24/19 Butyl Ether Silsesquioxane, Polydimethylsiloxy PPG-13 Butyl Ether Silsesquioxane, Polyglyceryl-3 Disiloxane Dimethicone, Polyglyceryl-3/Lauryl Polydimethylsiloxyethyl Dimethicone Crosspolymer, Polyglyceryl-3 Polydimethylsiloxyethyl Dimethicone, Poly(Glycol Adipate)/Bis-Hydroxyethoxypropyl Dimethicone Copolymer, Polymethylsilsesquioxane, Polymethylsilsesquioxane/Trimethylsiloxysilicate, Polyphenylsilsesquioxane, Polypropylsilsesquioxane, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, Polysilicone-19, Polysilicone-20, Polysilicone-21, Polysilicone-18 Cetyl Phosphate, Polysilicone-1 Crosspolymer, Polysilicone-18 Stearate, Polyurethane-10, Potassium Dimethicone PEG-7 Panthenyl Phosphate, Potassium Dimethicone PEG-7 Phosphate, PPG-12 Butyl Ether Dimethicone, PPG-2 Dimethicone, PPG-12 Dimethicone, PPG-27 Dimethicone, PPG-4 Oleth-10 Dimethicone, Propoxytetramethyl Piperidinyl Dimethicone, Propyl Trimethicone, Quaternium-80, Retinoxytrimethylsilane, Silanediol Salicylate, Silanetriol, Silanetriol Arginate, Silanetriol Glutamate, Silanetriol Lysinate, Silanetriol Melaninate, Silanetriol Trehalose Ether, Silica, Silica Dimethicone Silylate, Silica Dimethyl Silylate, Silica Silylate, Silicon Carbide, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, SiliconeQuaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, Silicone Quaternium-25, Siloxanetriol Alginate, Siloxanetriol Phytate, Simethicone, Sodium Carboxydecyl PEG-8 Dimethicone, Sodium Dimethicone PEG-7 Acetyl Methyltaurate, Sodium Hyaluronate Dimethylsilanol, Sodium Lactate Methylsilanol, Sodium Mannuronate Methylsilanol, Sodium PCA Methylsilanol, Sodium PG-Propyldimethicone Thiosulfate Copolymer, Sodium PG-Propyl Thiosulfate Dimethicone, Sodium Propoxyhydroxypropyl Thiosulfate Silica, Sorbityl Silanediol, Soy Triethoxysilylpropyldimonium Chloride, Stearalkonium Dimethicone PEG-8 Phthalate, Stearamidopropyl Dimethicone, Steardimonium Hydroxypropyl Panthenyl PEG-7 Dimethicone Phosphate Chloride, Steardimonium Hydroxypropyl PEG-7 Dimethicone Phosphate Chloride, Stearoxy Dimethicone, Stearoxymethicone/Dimethicone Copolymer, Stearoxytrimethylsilane, Stearyl Aminopropyl Methicone, Stearyl Dimethicone, Stearyl/Lauryl Methacrylate Crosspolymer, Stearyl Methicone, Stearyl Triethoxysilanek, Stearyl Trimethicone, Styrene/Acrylates/Dimethicone Acrylate Crosspolymer, Styrene/Acrylates/Dimethicone Copolymer, TEA-Dimethicone PEG-7 Phosphate, Tetrabutoxypropyl Trisiloxane, Tetramethyl Hexaphenyl Tetrasiloxane, Tetramethyl Tetraphenyl Trisiloxane, Tocopheryloxypropyl Trisiloxane, Trideceth-9 PG-Amodimethicone, Triethoxycaprylylsilane, Triethoxysilylethyl Dimethicone/Methicone Copolymer, Triethoxysilylethyl Polydimethylsiloxyethyl Dimethicone, Triethoxysilylethyl Polydimethylsiloxyethyl Hexyl Dimethicone, Triethoxysilylpropylcarbamoyl Ethoxypropyl Butyl Dimethicone, Trifluoromethyl C1-4 Alkyl Dimethicone, Trifluoropropyl Cyclopentasiloxane, Trifluoropropyl Cyclotetrasiloxane, Trifluoropropyl Dimethicone, Trifluoropropyl Dimethicone/PEG-10 Crosspolymer, Trifluoropropyl Dimethicone/Trifluoropropyl Divinyldimethicone Crosspolymer, Trifluoropropyl Dimethicone/Vinyl Trifluoropropyl, Dimethicone/Silsesquioxane Crosspolymer, Trifluoropropyl Dimethiconol, Trifluoropropyldimethyl/trimethylsiloxysilicate, Trifluoropropyl Methicone, Trimethoxycaprylylsilane, Trimethoxysilyl Dimethicone, Trimethyl Pentaphenyl Trisiloxane, Trimethylsiloxyamodimethicone, Trimethylsiloxyphenyl Dimethicone, Trimethylsiloxysilicate, Trimethylsiloxysilicate/Dimethicone Crosspolymer, Trimethylsiloxysilicate/Dimethiconol Crosspolymer, Trimethylsiloxysilylcarbamoyl Pullulan, Trimethylsilyl Hydrolyzed Conchiolin Protein PG-Propyl Methylsilanediol Crosspolymer, Trimethylsilyl Hydrolyzed Silk PG-Propyl Methylsilanediol Crosspolymer, Trimethylsilyl Hydrolyzed Wheat Protein PG-Propyl Methylsilanediol Crosspolymer, Trimethylsilyl Pullulan, Trimethylsilyl Trimethylsiloxy Glycolate, Trimethylsilyl Trimethylsiloxy Lactate, Trimethylsilyl Trimethylsiloxy Salicylate, Triphenyl Trimethicone, Trisiloxane, Tris-Tributoxysiloxymethylsilane, Undecylcrylene Dimethicone, Vinyl Dimethicone, Vinyl Dimethicone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer, VP/Dimethiconylacrylate/Polycarbamyl/Polyglycol Ester, Zinc Carboxydecyl Trisiloxane and Zinc Dimethicone PEG-8 Succinate and mixtures thereof.

More preferably the silicones to be contained in the mixture according to the inventions are Dimethicone, Cyclomethicone, Phenyl Trimethicone, Cyclohexasiloxane and Cyclopentasiloxane. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

1,2-Alkanediols

In a particular preferred embodiment the compositions may contain 1,2-alkanediols having up to 12 carbon atoms, such as 1,2-pentane diol, 1,2-hexanediol, 1,2-octanediol, 1,2-decanediol, a mixture of 1,2-hexanediol and 1,2-octanediol, a mixture of 1,2-hexanediol and 1,2-decanediol, a mixture of 1,2-octanediol and 1,2-decanediol, a mixture of 1,2-hexanediol, 1,2-octanediol and 1,2-decanediol, preferably in amounts of from 0.1 to about 10 and preferably from about 1 to about 8 percent by weight.

Fatty Alcohols

The compositions may also encompass fatty alcohols having 6 to 30 C atoms. The fatty alcohols here can be saturated or unsaturated and linear or branched. Furthermore, these fatty alcohols can in some cases be part of the oil phase (III) if they correspond to the definition given there. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and also Guerbet alcohols thereof, such as, for example, 2-octyl-1-dodecanol, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as beef tallow, peanut oil, colza oil, cottonseed oil, soya oil, sunflower oil, palm kernel oil, linseed oil, maize oil, castor oil, rapeseed oil, sesame oil, cacao butter and coconut fat, can further be employed.

Additional UV Filters and Primary Sun Protection Factors

In another preferred embodiment the compositions may contain additional UV filters. Suitable UV filters are, for example, organic UV absorbers from the class of 4-aminobenzoic acid and derivatives, benzophenone derivatives, salicylate derivatives, diphenylacrylates, 3-imidazol-4-ylacrylic acid and its esters, benzofuran derivatives, benzylidenemalonate derivatives, polymeric UV absorbers containing one or more organosilicon radicals, cinnamic acid derivatives, camphor derivatives, trianilino-s-triazine derivatives, 2-hydroxyphenylbenzotriazole derivatives, menthyl anthranilate, benzotriazole derivatives, merocyanine dye derivative e.g., Methoxy Propylamino Cyclohexenylidene Ethoxyethyl Cyanoacetate and indole derivatives. Specific additional UV filters which can be used are for example as follows:

Suitable UVA filters are for example the following:
Terephthalylidenedibornanesulphonic acid and salts (Mexoryl® SX);
Hexyl 2-(4-diethylamino-2-hydroxybenzoyl)benzoate (Uvinul® A Plus);
2,2'-(1,4-phenylene)bis-[1H-benzimidazole-4,5-disulfonic acid], disodium salt (Neo Heliopan® AP);
Menthyl anthranilate (Neo Heliopan® MA);
Suitable UVB filters encompass:
p-Aminobenzoic acid;
Ethyl p-aminobenzoate (25 mol) ethoxylated;
2-ethylhexyl p-dimethylaminobenzoate;
2-ethylhexyl p-methoxycinnamate (Neo Heliopan® AV);
Isoamyl p-methoxycinnamate (Neo Heliopan® E 1000);
Triethanolamine salicylate (Neo Heliopan® TS);
2-phenylbenzimidazole sulfonic acid (Neo Heliopan® Hydro) and its salts;
3-(4'-trimethylammonium)benzylidenebornan-2-one methyl sulphate;
3-(4'-sulpho)benzylidenebornan-2-one and salts;
3-(4'-methylbenzylidene)-d,l-camphor (Neo Heliopan® MBC);
N-[(2 and 4)-[2-(oxoborn-3-ylidene)methyl]benzyl]acrylamide polymer;
4,4'-[(6-[4-(1,1-dimethyl)aminocarbonyl)phenylamino]-1,3,5-triazine-2,4-diyl)diimino] bis(benzoic acid 2-ethylhexyl ester) (Uvasorb® HEB);
Benzylidenemalonate-polysiloxane (Parsol® SLX);
Tris(2-ethylhexyl)4,4',4"-(1,3,5-triazine-2,4,6-triyltriimino)tribenzoate (Uvinul® T150)
Methoxy Propylamino Cyclohexenylidene Ethoxyethyl Cyanoacetate
Suitable broadband filters are for example:
2-hydroxy-4-methoxybenzophenone-5-sulfonic acid (sulisobenzone, benzophenone-4) or its salts;
2-hydroxy-4-methoxybenzophenone (Neo Heliopan® BB, Oxybenzone, benzo-phenone-3);
Disodium 2,2'-dihydroxy-4,4'-dimethoxy-5,5'-disulphobenzophenone;
Phenol,-(2H-benzotriazol-2-yl-4-methyl-6-(2-methyl-3-(1,3,3,3-tetra methyl-1-(trimethylsilyl)oxy)disiloxanyl)propyl), (Mexoryl® XL);
2,2'-methylenebis(6-(2H-benztriazol-2-yl)-4-1,1,3,3-tetramethylbutyl)-phenol), Tinosorb® M);

Tris-Biphenyl Triazine (Tinosorb® A2B);

2,4-bis[[(3-(2-propyloxy)-2-hydroxypropyloxy)-2-hydroxy]phenyl]-6-(4-methoxy-phenyl)-1,3,5-triazine;

2,4-bis[[4-(2-ethylhexyloxy)-2-hydroxy]phenyl]-6-[4-(2-methoxyethyl-carbonyl)-phenylamino]-1,3,5-triazine;

2,4-bis[[4-(3-(2-propyloxy)-2-hydroxypropyloxy)-2-hydroxy]phenyl]-6-[4-(2-ethylcarboxyl)phenylamino]-1,3,5-triazine;

2,4-bis[[4-(2-ethylhexyloxy)-2-hydroxy]phenyl]-6-(1-methylpyrrol-2-yl)-1,3,5-triazine;

2,4-bis[[4-tris(trimethylsiloxysilylpropyloxy)-2-hydroxy]phenyl]-6-(4-methoxyphenyl)-1,3,5-triazine;

2,4-bis[[4-(2"-methylpropenyloxy)-2-hydroxy]phenyl]-6-(4-methoxyphenyl)-1,3,5-triazine;

2,4-bis[[4-(1',1',1',3',5',5',5'-heptamethylsiloxy-2"-methylpropyloxy)-2-hydroxy]-phenyl]-6-(4-methoxyphenyl)-1,3,5-triazine; and (5,6,5',6'-tetraphenyl-3,3'-(1,4-Phenylene)bis(1,2,4-triazine).

It is possible, furthermore, to use additional particulate UV filters or inorganic pigments, which if desired may have been rendered hydrophobic, such as the oxides of zinc (ZnO), of oxides of titanium (TiO2) of iron (Fe2O3), of zirconium (ZrO2), of silicon (SiO2), of manganese (e.g. MnO), of aluminium (Al2O3), of cerium (e.g. Ce2O3) and/or mixtures in amounts from 0.5% to 25%

In one embodiment according to the invention the total amount of oil soluble UV filters that can be used, which are, for example but not limited to avobenzone, and/or 2-ethylhexyl 4-dimethylaminobenzoate, and/or meradimate, and/or 2-ethylhexyl salicylate, and/or homosalate, and/or octinoxate, and/or isoamyl p-methoxycinnamate, and/or octocrylene, and/or methyl benzylidene camphor, and/or Uvasorb HEB, and/or Uvinul A Plus, and/or Mexoryl XL, and/or Benzophenone-3 and/or Parsol SLX, and/or Bemotrizinol, and/or Methoxy Propylamino Cyclohexenylidene Ethoxyethyl Cyanoacetate is in the range of 0.1 to 55% by weight, particularly in the range of 0.5 to 40% by weight, most particularly in the range of 1 to 30% by weight, based on the total weight of the composition.

In one embodiment according to the invention the amount of octinoxate or isoamyl p-methoxycinnamate when used as additional UV filters is in the range of 0.1 to 20.0% by weight, preferably in the range from 0.3 to 15% by weight and most preferably in the range from 0.5 to 10.0% by weight, based on the total weight of the composition.

In one embodiment according to the invention the amount of octocrylene is in the range of 0.1 to 20.0% by weight, preferably in the range from 0.3 to 15% by weight and most preferably in the range from 0.5 to 10.0% by weight, based on the total weight of the composition.

In one embodiment according to the invention the amount of salicylate esters is in the range of 0.1 to 20.0% by weight, preferably in the range from 0.3 to 15% by weight and most preferably in the range from 0.5 to 10.0% by weight, based on the total weight of the composition.

When Octisalate is chosen as the UV filter, it is advantageous that its total amount ranges from 0.1 to 5.0% by weight, based on the total weight of the composition. When Homosalate is chosen as the UV filter it is advantageous that its total amount ranges from 0.1 to 15.0% by weight, based on the total weight of the composition.

In one embodiment according to the invention the amount of Avobenzone is in the range of 0.1 to 10.0% by weight, preferably in the range from 0.3 to 7.0% by weight and most preferably in the range from 0.5 to 5.0% by weight, based on the total weight of the composition.

In one embodiment according to the invention the amount of Ensulizole when used as an additional UV filter is in the range of 0.1 to 10.0% by weight, preferably in the range from 0.3 to 8.0% by weight and most preferably in the range from 0.5 to 5.0% by weight, based on the total weight of the composition.

In one embodiment according to the invention the amount of Bemotrizinol is in the range of 0.1 to 10.0% by weight, preferably in the range from 0.3 to 7.0% by weight and most preferably in the range from 0.5 to 5.0% by weight, based on the total weight of the composition.

In one embodiment according to the invention the total amount of micro fine organic and/or inorganic pigments, for example but not limited to Zinc Oxide (coated and un-coated), and/or titanium dioxide (coated or un-coated) that may be used when used as additional UV filters in compositions according to the invention can be in the range of 0.1 to 35% by weight, preferably in the range from 0.3 to 25% by weight and more preferably in the range from 0.5 to 20.0% by weight and most preferably in the range from 0.75% to 10.0% by weight, based on the total weight of the composition. When titanium dioxide is chosen as the UV filter, it is advantageous that its total amount ranges from 0.1% to 20.0% by weight, based on the total weight of the composition. When Zinc Oxide is chosen as the UV filter, it is advantageous that its total amount ranges from 0.1% to 20.0% by weight, based on the total weight of the composition.

The amount of Uvasorb HEB when used as an additional UV filter according to the invention, is in the range of 0.1 to 10.0%, preferably in the range from 0.3 to 7.0% and most preferably in the range from 0.5 to 5.0% of the total formulation.

The amount of Uvinul T-150 when used as an additional UV filter according to the invention, is in the range of 0.1 to 10.0%, preferably in the range from 0.3 to 7.0% and most preferably in the range from 0.5 to 5.0% of the total formulation.

In one embodiment according to the invention the total amount of organic insoluble particulate UV filters when used as an additional UV filters according to the invention, which are, for example but not limited to 2,2'-methylenebis(6-(2H-benzotriazol-2-yl)-4-1,1,3,3-tetramethyl-butyl)-phenol), (Tinosorb M), Tris-Biphenyl Triazine (Tinosorb® A2B) and (5,6,5',6'-tetraphenyl-3,3'-(1,4-Phenylene)bis(1,2,4-triazine) is in the range of 0.5 to 5% of the total formulation.

The amount of 2,2'-methylenebis(6-(2H-benzotriazol-2-yl)-4-1,1,3,3-tetramethyl-butyl)-phenol), (Tinosorb M) when used as an additional UV filter according to the invention is in the range of 0.1 to 10.0%, preferably in the range from 0.3 to 7.0% and most preferably in the range from 0.5 to 5.0% of the total formulation.

The amount of Tris-Biphenyl Triazine (Tinosorb® A2B), when used as an additional UV filter according to the invention, is in the range of 0.1 to 10.0%, preferably in the range from 0.3 to 7.0% and most preferably in the range from 0.5 to 5.0% of the total formulation.

The amount of benzylidenemalonate-polysiloxane (Parsol® SLX) when used as an additional UV filter according to the invention, is in the range of 0.1 to 10.0%, preferably in the range from 0.3 to 7.0% and most preferably in the range from 0.5 to 5.0% of the total formulation.

In one embodiment of the invention the total amount of all sulfonated water soluble UV filters when used as an additional UV filters, like for example but not limited to, phenylbenzimidazole sulfonic acid, and/or Disodium Phenyl Dibenzimidazole Tetrasulphonic Acid and/or Benzophenone-4, and/or terephthalylidenedibornanesulphonic and/or 3-(4'-trimethylammonium)benzylidenebornan-2-one methyl sulphate, and/or 3-(4'-sulpho)benzylidenebornan-2-one, and their salts in cosmetic and pharmaceutical preparations, preferably dermatological preparations, are in the range of 0.1 to 15.0% and more particularly in the range from 0.5 to 10.0% and most particularly in the range of 1.0 to 8.0% of the total formulation.

The amount of disodium phenyl dibenzimidazole tetrasulfonate and its salts when used as an additional UV filter according to the invention, is in the range of 0.1 to 10.0%, preferably in the range from 0.3 to 8% and most preferably in the range from 0.5 to 5.0% of the total formulation.

The amount of phenylbenzimidazole sulfonic acid and its salts when used as an additional UV filter according to the invention, is in the range of 0.1 to 10.0%, preferably in the range from 0.3 to 8% and most preferably in the range from 0.5 to 5.0% of the total formulation.

The amount of Mexoryl SX and its salts when used as an additional UV filter according to the invention is in the range of 0.1 to 10.0%, preferably in the range from 0.3 to 8% and most preferably in the range from 0.5 to 5.0% of the total formulation.

In another preferred embodiment the compositions further comprise at least one additional UVA filter selected from the group consisting of:
Terephthalylidenedibornanesulphonic acid and salts (Mexoryl® SX),
Hexyl 2-(4-diethylamino-2-hydroxybenzoyl)benzoate (Uvinul® A Plus),
Menthyl anthranilate (Neo Heliopan® MA),
2,2'-(1,4-phenylene)bis-[1H-benzimidazole-4,5-disulfonic acid], disodium salt (Neo Heliopan® AP),
and mixtures thereof.

In another preferred embodiment the compositions further comprise at least one additional UVB filter selected from the group consisting of:
2-ethylhexyl p-dimethylaminobenzoate;
Triethanolamine salicylate (Neo Heliopan® TS);
2-ethylhexyl p-methoxycinnamate (Neo Heliopan® AV);
Isoamyl p-methoxycinnamate (Neo Heliopan® E 1000);
2-phenyl benzimidazole sulfonic acid (Neo Heliopan® Hydro) and its salts
3-(4'-methylbenzylidene)-d,l-camphor (Neo Heliopan® MBC)
4,4'-[(6-[4-(1,1-dimethyl)aminocarbonyl)phenylamino]-1,3,5-triazine-2,4-diyl)diimino] bis(benzoic acid 2-ethyl hexyl ester) (Uvasorb® HEB);
Benzylidenemalonate-polysiloxane (Parsol® SLX);
(Tris(2-ethylhexyl)4,4',4''-(1,3,5-triazine-2,4,6-triyl-triimino)tribenzoate (Uvinul® T150);
Methoxy Propylamino Cyclohexenylidene Ethoxyethyl Cyanoacetate;
and mixtures thereof.

In another preferred embodiment the compositions further comprises at least one additional broadband filter selected from the group consisting of:
2-hydroxy-4-methoxybenzophenone-5-sulfonic acid (sulisobenzone, benzophenone-4) or its salts.
2-hydroxy-4-methoxybenzophenone (Neo Heliopan® BB, Oxybenzone, benzophenone-3)
Phenol,-(2H-benzotriazol-2-yl-4-methyl-6-(2-methyl-3-(1,3,3,3-tetra methyl-1-(trimethylsilyl)oxy)disiloxanyl)propyl), (Mexoryl® XL)
2,2'-methylenebis(6-(2H-benztriazol-2-yl)-4-1,1,3,3-tetramethylbutyl)-phenol), Tinosorb® M)
Tris-Biphenyl Triazine (Tinosorb® A2B);
(5,6,5',6'-tetraphenyl-3,3'-(1,4-Phenylene)bis(1,2,4-triazine);
and mixtures thereof.
indanylidene compounds in accordance with DE 10055940 (=WO 02/38537).

Advantageous primary and also secondary sun protection ingredients are mentioned in WO 2005123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Ingredients

Besides the groups of primary sun protection ingredients mentioned above, secondary sun protection ingredients of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Pigments

Advantageous inorganic secondary light protection factors are pigments, preferably inorganic pigments based on finely disperse metal oxides and/or other metal compounds which are insoluble or sparingly soluble in water, in particular the oxides of titanium (TiO$_2$), zinc (ZnO), iron (e.g. Fe$_2$O$_3$), zirconium (ZrO$_2$), silicon (SiO$_2$), manganese (e.g. MnO), aluminum (Al$_2$O$_3$), cerium (e.g. Ce$_2$O$_3$), mixed oxides of the corresponding metals, and mixtures of such oxides. These pigments are X-ray-amorphous or non-X-ray-amorphous. X-ray-amorphous oxide pigments are metal oxides or semi-metal oxides which reveal no or no recognizable crystalline structure in X-ray diffraction experiments. Such pigments are often obtainable by flame reaction, for example by reacting a metal or semi-metal halide with hydrogen and air (or pure oxygen) in a flame.

X-ray-amorphous oxide pigments are used as thickeners and thixotropic agents, flow auxiliaries for emulsion and dispersion stabilization and as carrier substance (for example for increasing the volume of finely divided powders). X-ray-amorphous oxide pigments which are known and often used in cosmetic or dermatological galenics are, for example, high-purity silicon oxide. Preference is given to high-purity, X-ray-amorphous silicon dioxide pigments with a particle size in the range from 5 to 40 nm and an active surface area (BET) in the range from 50 to 400 m$^2$/g, preferably 150 to 300 m$^2$/g, where the particles are to be regarded as spherical particles of very uniform dimension. Macroscopically, the silicon dioxide pigments are recognizable as loose, white powders. Silicon dioxide pigments are sold commercially under the name Aerosil® (CAS-No. 7631-85-9) or Carb-O-Sil Advantageous Aerosil® grades are, for example, Aerosil®0X50, Aerosil®130, Aerosil®150, Aerosil®200, Aerosil®300, Aerosil®380, Aerosil® MQX 80, Aerosil® MOX 170, Aerosil® COK 84, Aerosil® R 202, Aerosil® R 805, Aerosil® R 812, Aerosil® R 972, Aerosil® R 974, Aerosil® R976.

The compositions according to the present invention can comprise 0.1 to 20% by weight, advantageously 0.5 to 10% by weight, more preferably 1 to 5% by weight, based on the total weight of the compositions, of X-ray-amorphous oxide pigments.

The non-X-ray-amorphous inorganic pigments are, according to the present invention, advantageously in hydrophobic form, i.e. have been surface-treated to repel water. This surface treatment may involve providing the pigments with a thin hydrophobic layer by processes known per se. Such a process involves, for example, producing the hydrophobic surface layer by a reaction according to

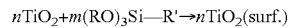

$n$TiO$_2$+$m$(RO)$_3$Si—R'→$n$TiO$_2$(surf.)

where n and m are stoichiometric parameters to be used as desired, and R and R' are the desired organic radicals. Hydrophobic pigments prepared analogously to DE-A 3314742, for example, are advantageous.

Preferably the compositions comprise pigments selected from zinc oxide and titanium dioxide or their mixtures.

The total amount of inorganic pigments, in particular hydrophobic inorganic micro pigments, in the finished cosmetic, dermatological and pharmacological composition according to the invention can be advantageously chosen from the range from 0.1 to 30% by weight, preferably 0.1 to 10.0% by weight, preferably 0.5 to 6.0% by weight, based on the total weight of the compositions.

Antioxidants

An additional content of antioxidants in the compositions of the present invention is generally preferred. According to the present invention, favorable antioxidants which can be used are all antioxidants customary or suitable for cosmetic, dermatological and pharmacological preparations. The antioxidants are advantageously chosen from the group of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxy-toluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), derivatives of acetophenone such as Hydroxyacetophenone and its blends with Phenoxyethanol and/or, pentane 1,2 diol and/or hexane 1,2 diol and/or caprylyl 1,2 diol, are suitable according to the present invention.

The amount of the above-mentioned antioxidants (one or more compounds) in the composition is preferably 0.001 to 30% by weight, more preferably 0.05 to 20% by weight, and most preferably 1 to 10% by weight, based on the total weight of the composition.

Vitamins

In a preferred embodiment the composition of the invention may advantageously also comprise vitamins and vitamin precursors, it being possible for all the vitamins and vitamin precursors which are suitable or usual for cosmetic and/or dermatological applications to be used. Those worth mentioning here are, in particular, vitamins and vitamin precursors, such as tocopherols, vitamin A, niacin acid and niacinamide, further vitamins of the B complex, in particular biotin, and vitamin C and panthenol and derivatives thereof, in particular the esters and ethers of panthenol, and cationically derivatized panthenols, such as panthenol triacetate, panthenol monoethyl ether and the monoacetate thereof and cationic panthenol derivatives. If vitamin E and/or derivatives thereof represent the antioxidant(s), it is advantageous to choose their respective concentrations from the range from 0.001 to 10% by weight, based on the total weight of the composition. If vitamin A or vitamin A derivatives, or carotenes or derivatives thereof represent the antioxidant(s), it is advantageous to choose their respective concentrations from the range from 0.001 to 10% by weight, based on the total weight of the composition.

Plant Extracts

The compositions may also include plant extracts, which are conventionally prepared by extraction of the whole plant, but also in individual cases exclusively from blossom and/or leaves, wood, bark or roots of the plant. In respect of the plant extracts which can be used, reference is made in particular to the extracts which are listed in the table starting on page 44 of the 3rd edition of the Leitfaden zur Inhaltsstoffdeklaration kosmetischer Mittel [Manual of Declaration of the Constituents of Cosmetic Compositions], published by Industrieverband Körperpflegemittel and Waschmittel e.V. (IKW), Frankfurt. Extracts which are advantageous in particular are those from aloe, witch hazel, algae, oak bark, rose-bay willow-herb, stinging nettle, dead nettle, hops, chamomile, yarrow, arnica, calendula, burdock root, horsetail, hawthorn, linden blossom, almond, pine needle, horse chestnut, sandalwood, juniper, coconut, mango, apricot, orange, lemon, lime, grapefruit, apple, green tea, grapefruit pip, wheat, oats, barley, sage, thyme, wild thyme, rosemary, birch, mallow, lady's smock, willow bark, restharrow, coltsfoot, hibiscus, ginseng and ginger root.

In this context, the extracts from aloe vera, chamomile, algae, rosemary, calendula, ginseng, cucumber, sage, stinging nettle, linden blossom, arnica and witch hazel are particularly preferred. Mixtures of two or more plant extracts can also be employed. Extraction agents which can be used for the preparation of plant extracts mentioned are, inter alia, water, alcohols and mixtures thereof. In this context, among the alcohols lower alcohols, such as ethanol and isopropanol, but also polyhydric alcohols, such as ethylene glycol, propylene glycol and butylene glycol, are preferred, and in particular both as the sole extraction agent and in mixtures with water. The plant extracts can be employed both in pure and in diluted form.

Skin Lightening Agents

An additional content of skin lightening ingredients in the compositions according to the present invention is also possible. Such skin lightening ingredients which can be used are for example but not limited to the following: kojic acid (5-hydroxy-2-hydroxymethyl-4-pyranone), kojic acid derivatives such as for example kojic dipalmitate, arbutin, ascorbic acid, ascorbic acid derivatives, hydroquinone, hydroquinone derivatives, styryl resorcinol derivatives (e.g. 4-(1-phenylethyl)1,3-benzenediol), molecules containing sulphur, such as glutathione or cysteine for example, alpha-hydroxy acids (e.g. citric acid, lactic acid, malic acid) and their derivatives, N-acetyltyrosine and derivatives, undecenoylphenylalanine, gluconic acid, chromone derivatives such as aloesin, flavonoids, thymol derivatives, 1-aminoethylphosphinic acid, thiourea derivatives, ellagic acid, nicotinamide, zinc salts such as zinc chloride or zinc gluconate for example, thujaplicin and derivatives, triterpenes such as maslic acid, sterols such as ergosterol, benzofuranones such as senkyunolide, vinyl- and ethylguaiacol, dionic acids such as octodecenedionic acid and azelaic acid, nitrogen oxide synthesis inhibitors such as L-nitroarginine and its derivatives, 2,7-dinitroindazole or thiocitrulline, metal chelators (e.g. alpha-hydroxy fatty acids, palmitic acid, phytic acid, lactoferrin, humic acid, gallic acid, bile extracts, bilirubin, biliverdin), retinoids, soja milk, soya extract, serine protease inhibitors or lipoic acid or other synthetic or natural active compounds for skin and hair lightening, these compounds also being used in the form of an extract from plants, such as bearberry extract, rice extract, papaya extract, liquorice root extract or constituents concentrated from these, such as glabridin or licochalcone A, *Artocarpus* extract, extract from *Rumex* and *Ramulus* species, extracts from pine species (*Pinus*) and extracts from *Vitis* species or stilbene derivatives concentrated from these, extract from saxifraga, mulberry, Scutelleria and/or grapes.

Actives Modulating Skin Pigmentation

Preferred active ingredients for hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, *Artocarpus* extract, extract of *Rumex* and *Ramulus* species, extracts of pine species (*Pinus*), extracts of *Vitis* species or stilbene derivatives isolated or concentrated therefrom, saxifrage extract, scutelleria extract, grape extract and/or microalgae extract, in particular Tetraselmis suecica Extract.

Advantageous skin tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, microalgae extracts, in particular *Isochrysis galbana*, trehalose, erythrulose and dihydroxyacetone. Flavonoids which bring about skin and hair tinting or browning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(-)-isopulegol, I-(-)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Inflammatory Agents

The compositions may also comprise active anti-inflammatory and/or redness- and/or itching-alleviating compounds (anti-irritants). All the active anti-inflammatory or redness- and/or itching-alleviating compounds which are suitable or usual for cosmetic, dermatological and pharmacological compositions can be used here. Active anti-inflammatory and redness- and/or itching-alleviating compounds which are advantageously employed are steroidal anti-inflammatory substances of the corticosteroid type, such as hydrocortisone, dexamethasone, dexamethasone phosphate, methylprednisolone or cortisone, it being possible for the list to be extended by addition of further steroidal anti-inflammatories. Non-steroidal anti-inflammatories can also be employed. Those to be mentioned here by way of example are oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropazone.

Alternatively, natural anti-inflammatory or redness- and/or itching-alleviating substances can be employed. Plant extracts, specific highly active plant extract fractions and highly pure active substances isolated from plant extracts can be employed. Extracts, fractions and active substances from chamomile, aloe vera, *Commiphora* species, *Rubia* species, willow, rose-bay willow-herb, oats, and also pure substances, such as, inter alia, bisabolol, apigenin 7-glucoside, boswellic acid, phytosterols, glycyrrhizic acid, glabridin or licochalcone A, are particularly preferred. The compositions of the present invention can also comprise mixtures of two or more active anti-inflammatory compounds. Bisabolol, boswellic acid, and also extracts and isolated highly pure active compounds from oats and *Echinacea* are particularly preferred for use in the context of the invention as anti-inflammatory and redness- and/or itching-alleviating substances, and alpha-bisabolol and extracts and isolated highly pure active compounds from oats are especially preferred.

Preferred anti-inflammatory agents may be selected from the group formed by:

(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone, (ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone, (iii) natural or naturally occurring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof, (iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

The amount of anti-irritants (one or more compounds) in the composition is preferably 0.0001% to 20% by weight, with particular preference 0.0001% to 10% by weight, in particular 0.001% to 5% by weight, based on the total weight of the composition.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-yl methyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers, Hydrotropes and Moist Retention Regulators

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preferred moist retention regulators encompass sodium lactate, urea, alcohols, sorbitol, glycerol, propylene glycol, aliphatic 1,2-diols with a C number of 5-10, collagen, elastin or hyaluronic acid, diacyl adipates, petrolatum, ectoin, urocanic acid, lecithin, panthenol, phytantriol, lycopene, algae extract, ceramides, cholesterol, glycolipids, chitosan, chondroitin sulphate, polyamino acids and polyamino sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids, such as betulinic acid or ursolic acid, algae extracts.

Preservatives

Suitable preservatives Preservatives which are preferably chosen here are those such as benzoic acid, its esters and salts, propionic acid and its salts, salicylic acid and its salts, 2,4-hexadienoic acid (sorbic acid) and its salts, formaldehyde and paraformaldehyde, 2-hydroxybiphenyl ether and its salts, 2-zincsulphidopyridine N-oxide, inorganic sulphites and bisulphites, sodium iodate, chlorobutanolum, 4-ethylmercuryl(II)-5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioximidazolidin-5-yl)urea), poly(hexamethylene diguanide) hydrochloride, 2-phenoxyethanol, hexamethylenetetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, benzyl alcohol, octopirox, 1,2-dibromo-2,4-dicyanobutane, 2,2'-methylenebis(6-bromo-4-chlorophenol), bromochlorophene, mixture of 5-chloro-2-methyl-3(2H)-isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and its salts, glutaraldehyde, 5-ethyl-1-aza-3,7-dioxabicyclo[3.3.0]octane, 3-(4-chlorophenoxy)-1,2-propanediol, hyamines, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethylbenzyl-ammonium saccharinate, benzyl hemiformal, 3-iodo-2-propynyl butylcarbamate, sodium hydroxymethylaminoacetate or sodium hydroxymethylaminoacetate.

In various cases it may also be advantageous to employ substances which are chiefly employed for inhibition of the growth of undesirable microorganisms on or in animal organisms in compositions of the invention. In this respect, in addition to conventional preservatives, further active compounds which are worth mentioning, in addition to the large group of conventional antibiotics, are, in particular, the products relevant for cosmetics, such as triclosan, climbazol, octoxyglycerol, octopirox (1-hydroxy-4-methyl-6-(2,4,4-trimethylpentyl)-2(1H)-pyridone, 2-aminoethanol), chitosan, farnesol, glycerol monolaurate or combinations of the substances mentioned, which are employed, inter alia, against underarm odour, foot odour or dandruff formation. Also ingredients which have multifunctional properties including the ability to reduce the growth of bacteria, yeast and molds may be employed to compositions covered by the invention. These may include, but are not restricted to pentane 1,2-diol, hexane 1,2-diol, caprylyl 1,2-diol, decyl 1,2-diol, tropolone, hydroxyacetophenone, ethylhexyl glycerin, phenoxyethanol either as individual ingredients or a mixtures of 2 or more of these.

Furthermore, the compositions of the invention may also comprise substances having a cooling action. Individual active cooling compounds which are preferred for use in the context of the present invention are listed below. The skilled person is able to supplement the following list with a large number of further active cooling compounds; the active cooling compounds listed can also be employed in combination with one another: 1-menthol, d-menthol, racemic menthol, menthone glycerol acetal (trade name: Frescolat® MGA), menthyl lactate (trade name: Frescolat® ML, menthyl lactate is preferably I-menthyl lactate, in particular 1-menthyl 1-lactate), menthyl ethylamido oxalate (Frescolat® X-Cool), substituted menthyl-3-carboxylic acid amides (e.g. menthyl-3-carboxylic acid N-ethylamide), 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclo-hexanone glycerol ketal, 3-menthyl 3,6-di- and -trioxaalkanoates, 3-menthyl methoxyacetate, icilin.

In a particular preferred embodiment the compositions may comprise preservatives chosen from 4-hydroxyacetophenone, o-cymen-5-ol or mixtures thereof.

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, β-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3Fe_3O_4$, FeO(OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced). Preferably the compositions represent emulsions and alcoholic sprays.

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

In a preferred embodiment the compositions represent emulsions (i) encompassing an oil phase comprising additives selected from the group consisting of hydrocarbon oils, waxes, silicone oils, natural oils, fatty acid esters, fatty alcohols, antioxidants, chelating agents, skin lightening agents, tan accelerating agents, insect repelling agents, moisturizing agents, water resistant polymers, and mixtures thereof, and/or (b) encompasses an aqueous phase comprising additives selected from the group consisting of antioxidants, preservation agents, chelating agents, and mixtures thereof.

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

In a further preferred embodiment according to the invention the composition has a UVA protection factor of at least 370 nm, as measured by the Critical Wavelength Method for in vitro determination of UVA protection. The critical wavelength is defined as the wavelength at which the integral of the spectral absorbance curve reaches 90% of the integral over the UV spectrum from 290 to 400 nm. The method of its determination is described in the United States Federal Register FR volume 77, No. 92, Jun. 17, 2011 pages 35664-3565. The minimum critical wavelength allowed to fulfil the broad spectrum protection claim is 370 nm.

In a further preferred embodiment according to the invention the composition is used in a cosmetic, pharmaceutical or dermatological composition, more preferred a dermatological active composition.

A method for obtaining the composition is to mix together in a suitable container Avobenzone, Bemotrizinol, Octocrylene, Homosalate and Octisalate.

Furthermore, a method for using the composition according to the invention is provided herein, comprising the following steps:

(a) providing at least one oil phase comprising the mixture of Avobenzone, Bemotrizinol, Octocrylene, Homosalate and Octisalate;

(c) homogenizing each of said oil phase and said aqueous phase separately;

(d) adding said aqueous phase to said oil phase to a mixture or vice versa; and (e) homogenizing said mixture.

In one embodiment according to the invention, the oil phase and the aqueous phase are added together at ambient temperature.

In one embodiment according to the invention, the oil phase and the aqueous phase are heated before step (c) to temperatures between 70 and 90° C.

In another embodiment of the invention oil phase can be kept at ambient temperature and the aqueous phase heated to between 70 and 90° C. before step (c).

In a further embodiment of the invention the aqueous phase can be heated to between 70 and 90° C. and the oil phase kept at ambient temperature before step (c)

INDUSTRIAL APPLICATION

Another object of the present invention refers to a non-therapeutic method for protecting human skin and hair against UV radiation comprising or consisting of the following steps:

(i) providing either the blend or a composition as defined above, and (ii) bringing either said blend or said composition in contact with said human skin or hair.

Finally, the present invention also encompasses the use either of the blend of or a composition as defined above for protecting human skin and hair against UV radiation.

For the sake of good order it is hereby stated that all preferred combinations and ranges including all preferred embodiments also count with regard to the method and the use as described above. Any repetition is therefore not necessary.

The following examples are intended to illustrate the present invention without restricting it. All amounts quoted, proportions and percentages are, unless indicated otherwise, based on the weight and the total amount or on the total weight of the compositions.

EXAMPLES

Preparation of a Blend "A" According to the Invention

TABLE 1

| Inventive Blend of UV filters (amounts in wt.-%) | |
|---|---|
| Ingredients | Amount |
| Butyl Methoxydibenzoylmethane | 13.50 |
| Octocrylene | 27.00 |
| Homosalate | 27.00 |
| Octisalate | 13.50 |
| Bemotrizinol | 19.00 |
| Total | 100.00 |

Add all of the components of table 1 to a suitable container and heat to 85° C. with continuous stirring until all the solids have dissolved. Cool down to ambient temperature and transfer to a holding vessel. The following formulation examples were prepared by incorporation of Blend A as explained above. All amounts are expressed in wt.-%.

FORMULATION EXAMPLES

Example 1

Sunscreen Lotion (O/W), Expected SPF 50+

| Phase | Ingredient | INCI or USAN name | 1A | 1B |
|---|---|---|---|---|
| A | Emulsiphos ® | Potassium Cetyl Phosphate, Hydrogenated Palm Glycerides | 2.00 | 2.00 |
| | Neo Heliopan ® 357 | Butyl Methoxydibenzoylmethane | 3.38 | 0.00 |

-continued

| Phase | Ingredient | INCI or USAN name | 1A | 1B |
|---|---|---|---|---|
| | Neo Heliopan ® 303 | Octocrylene | 6.75 | 0.00 |
| | Neo Heliopan ® OS | Ethylhexyl Salicylate | 3.38 | 0.00 |
| | Neo Heliopan ® HMS | Homosalate | 6.75 | 0.00 |
| | Neo Heliopan ® BMT | Bemotrizinol | 4.75 | 0.00 |
| | Blend A | Butyl Methoxydibenzoylmethane, Octocrylene, Ethylhexyl Salicylate, Homosalate, Bemotrizinol | 0.00 | 25.00 |
| | Cetyl Alcohol | Cetyl Alcohol | 1.00 | 1.00 |
| | PCL Liquid 100 | Cetearyl 2-Ethylhexanoate | 12.00 | 12.00 |
| | KP-545 L | Dimethicone (and) Acrylates/ Dimethicone Copolymer | 1.00 | 1.00 |
| | Edeta ® BD | Disodium EDTA | 0.10 | 0.10 |
| B | Aqua/Water | Aqua/Water | 53.49 | 53.49 |
| | Sodium Hydroxide, 10% aq. Solution | Aqua, Sodium Hydroxide | 0.50 | 0.50 |
| | Glycerin 99% | Glycerin | Ad 00 | Ad 100 |
| | Carbopol ® Ultrez 21 | Acrylates/C10-30 Alkyl Acrylate Crosspolymer | 0.20 | 0.20 |
| | Keltrol ® CG-BT | Xanthan Gum | 0.20 | 0.20 |
| | SymSave ® H | Hydroxyacetophenone | 0.50 | 0.50 |
| | Hydrolyte ® CG | Caprylyl Glycol | 0.25 | 0.25 |
| C | Fragrance | Perfume | qs | qs |
| In-Vitro SPF | | | 55 | 71 |
| In-Vitro UVA PF | | | 32 | 32 |
| Critical Wavelength (nm) | | | 379 | 379 |

Manufacturing Procedure

Add all components of phases A and B together except for the Carbopol® and Keltrol® and heat with stirring to 80° C. Then add the Carbopol® and Keltrol® with stirring. Homogenize with an Ultra Turrax® (13000 rpm/1 minutes per 100 g emulsion). Cool down to ambient temperature while stirring and add Phase C with stirring.

Alternative Manufacturing Procedure

Add all components of phase A together and heat to 85° C. with stirring until homogeneous. Add all components of phase B together without Sodium Hydroxide solution with stirring while heating to 80° C. Add Sodium Hydroxide solution with stirring. Add phase B to phase A with stirring, and homogenize with an Ultra Turrax® (13000 rpm/1 minutes per 100 g emulsion). Cool down to ambient temperature while stirring and add Phase C with stirring.

When 1.30 mg/cm² of the emulsion was spread onto PMMA plates as described in ISO 24443:2012 Determination of Sunscreen UVA Protection in-vitro and the absorbance curves of formulations 1A and 1B measured we observe that shape of the absorbance curves are very similar to that shown in dilute solution but very surprisingly we observe that the absorbance curve of formula 1B, which has used the premixed combination of UV filters, is significantly higher than that of formula 1A (FIG. 2) in which the UV filters were added individually to the formulation, resulting in a significantly higher SPF.

Example 2

Sunscreen Lotions (O/W)—Expected SPF 10, 20, 30 and 50

| Phase | Ingredient | INCI or USAN name | 2A | 2B | 2C | 2D |
|---|---|---|---|---|---|---|
| A | Emulsiphos ® | Potassium Cetyl Phosphate, Hydrogenated Palm Glycerides | 2.00 | 2.00 | 2.00 | 2.00 |
| | Blend A | Butyl Methoxydibenzoylmethane, Octocrylene, Ethylhexyl Salicylate, Homosalate, Bemotrizinol | 5.00 | 10.00 | 15.00 | 20.00 |
| | Cetyl Alcohol | Cetyl Alcohol | 1.00 | 1.00 | 1.00 | 1.00 |
| | PCL Liquid 100 | Cetearyl 2-Ethylhexanoate | 12.00 | 12.00 | 12.00 | 12.00 |
| | KP-545 L | Dimethicone (and) Acrylates/ Dimethicone Copolymer | 1.00 | 1.00 | 1.00 | 1.00 |
| | Edeta ® BD | Disodium EDTA | 0.10 | 0.10 | 0.10 | 0.10 |
| B | Aqua/Water | Aqua/Water | 73.49 | 68.49 | 63.49 | 58.49 |
| | Sodium Hydroxide, 10% aq. Soln | Aqua, Sodium Hydroxide | 0.50 | 0.50 | 0.50 | 0.50 |
| | Glycerin 99% | Glycerin | Ad 100 | | | |
| | Carbopol ® Ultrez 21 | Acrylates/C10-30 Alkyl Acrylate Crosspolymer | 0.20 | 0.20 | 0.20 | 0.20 |
| | Keltrol ® CG-BT | Xanthan Gum | 0.20 | 0.20 | 0.20 | 0.20 |
| | SymSave ® H | Hydroxyacetophenone | 0.50 | 0.50 | 0.50 | 0.50 |
| | Hydrolyte ® CG | Caprylyl Glycol | 0.25 | 0.25 | 0.25 | 0.25 |
| C | Fragrance | Perfume | qs | qs | qs | qs |
| In-Vitro SPF | | | 12 | 25 | 35 | 50 |
| In-Vitro UVA PF | | | 6 | 10 | 16 | 23 |
| Critical Wavelength (nm) | | | 373 | 375 | 376 | 378 |

Manufacturing Procedure

Add all components of phases A and B together except for the Carbopol® and Keltrol® and heat with stirring to 80° C. Then add the Carbopol® and Keltrol® with stirring. homogenise with an Ultra Turrax® (13000 rpm/1 minutes per 100 g emulsion). Cool down to ambient temperature while stirring and add Phase C with stirring.

Example 3

Cold-Cold Sunscreen Lotion (O/W)—Expected SPF 50

| Phase | Ingredient | INCI or USAN name | 3 |
|---|---|---|---|
| A | Dracorin® GOC | Gylceryl Oleate Citrate | 2.50 |
| | Described Mixture | Butyl Methoxydibenzoylmethane, Octocrylene, Ethylhexyl Salicylate, Homosalate, Bemotrizinol | 25.00 |
| | PCL Liquid 100 | Cetearyl 2-Ethylhexanoate | 12.00 |
| | KP-545 L | Dimethicone (and) Acrylates/Dimethicone Copolymer | 1.00 |
| | Edeta® BD | Disodium EDTA | 0.10 |
| B | Aqua/Water | Aqua/Water | 54.20 |
| | Glycerin 99% | Glycerin | Ad 00 |
| | Aristoflex® Velvet | Polyacrylate Cross Polymer 11 | 0.80 |
| | SymOcide® PS | Phenoxyethanol, Decylene Glycol, 1,2-Hexanediol | 1.40 |
| C | Fragrance | Perfume | qs |
| | In-Vitro SPF | | 51 |
| | In-Vitro UVA PF | | 20 |
| | Critical Wavelength (nm) | | 379 |

Manufacturing Procedure

Add all components of phases A and B except for the Aristoflex® Velvet without heating. Then add the Aristoflex® with stirring, and homogenize with an Ultra Turrax® (13000 rpm/1 minutes per 100 g emulsion). Add Phase C with stirring.

Example 4

Very Low Viscosity Sunscreen Lotions (O/W)—Expected SPF 50

| Phase | Ingredient | INCI or USAN name | 4A | 4B | 4C |
|---|---|---|---|---|---|
| A | Emulsiphos® | Potassium Cetyl Phosphate, Hydrogenated Palm Glycerides | 2.00 | 2.00 | 1.50 |
| | SymMollient® PDCC | Propylenediol Dicapylate Caprate | 7.00 | 7.00 | 7.00 |
| | Blend A | Butyl Methoxydibenzoylmethane, Octocrylene, Ethylhexyl Salicylate, Homosalate, Bemotrizinol | 25.00 | 25.00 | 25.00 |
| | Floraesters® K 100 Jojoba | Hydrolysed Jojoba ester (and) Jojoba Esters (and) water (Aqua) | 0.50 | 0.50 | 0.50 |
| | KP-545L | Dimethicone (and) Acrylates/Dimethicone Copolymer | 0.00 | 0.00 | 1.00 |
| | Edeta® BD | Disodium EDTA | 0.10 | 0.10 | 0.10 |
| B | Aqua/Water | Aqua/Water | | Ad 100 | |
| | Sodium Hydroxide, 10% aq. Soln | Aqua, Sodium Hydroxide | 0.30 | 1.00 | 0.30 |
| | L-Arginine | Arginine | 0.00 | 1.00 | 0.00 |
| | Neo Heliopan® Hydro | Phenylbenzimidazole Sulfonic Acid | 0.00 | 2.00 | 0.00 |
| | Keltrol® CC-BT | Xanthan Gum | 0.30 | 0.30 | 0.05 |
| | Keltrol® CG-SFT | Xanthan Gum | 0.05 | 0.05 | 0.30 |
| | SymSave® H | Hydroxyacetophenone | 0.50 | 0.50 | 0.50 |
| | Hydrolyte® CG | Caprylyl Glycol | 0.25 | 0.25 | 0.25 |
| | Hydrolyte® 5 Green | 1,2-Pentylene Glycol | 2.00 | 2.00 | 2.00 |
| C | Fragrance | Parfum | qs | qs | qs |
| | Vitacel CS 20 FC | Cellulose | 0.00 | 1.00 | 1.00 |
| | In-Vitro SPF | | 53 | 52 | 53 |
| | In-Vitro UVA PF | | 33 | 27 | 32 |
| | Critical Wavelength (nm) | | 379 | 375 | 379 |

Manufacturing Procedure

Add all components of phase A together and heat to 80° C. with stirring until homogeneous. Add the first four components of Phase B together with stirring until all of the Neo Heliopan Hydro® has dissolved. Add the rest of the components of phase B together with stirring while heating to 80° C. Add phase B to phase A with stirring, and homogenise with an Ultra Turrax® (13000 rpm/1 minutes per 100 g emulsion). Cool down to ambient temperature while stirring and add Phase C with stirring.

Example 5

Sunscreen Oils—Expected SPFs 50+ and 30

| Ingredient | INCI or USAN name | 5A | 5B |
|---|---|---|---|
| Blend A | Butyl Methoxydibenzoylmethane, Octocrylene, Ethylhexyl Salicylate, Homosalate, Bemotrizinol | 25.00 | 15.00 |
| Softisan® 100 | Hydrogenated Coco Glycerides | 10.00 | 10.00 |
| SymMollient® PDCC | Propylenediol Dicapylate Caprate | 10.00 | 10.00 |
| PCL Liquid 100 | Cetearyl 2-Ethylhexanoate | 10.00 | 10.00 |
| Neutral Oil | Capric Caprlyate Triglycerides | 31.00 | 31.00 |
| Isoadipate | Isopropyl Adipate | 5.00 | 10.00 |
| Isodragol® | Triisononanoin | 5.00 | 10.00 |
| SymMollient® S | Cetearyl Nonanoate | 3.00 | 3.00 |
| Hydrolyte® 5 Green | 1,2-Pentylene Glycol | Ad 100 | Ad 100 |
| Fragrance | Perfume | qs | qs |
| In-Vitro SPF | | 90 | 43 |
| In-Vitro UVA PF | | 25 | 15 |
| Critical Wavelength (nm) | | 379 | 379 |

Example 6

Cold-Cold Manufacture of Sunscreen Lotions—Expected SPF 50 and 50+

| Phase | Ingredient | INCI or USAN name | 6A | 6B |
|---|---|---|---|---|
| A | Dracorin® GOC | Gylceryl Oleate Citrate | 2.00 | 2.00 |
|  | Blend A | Butyl Methoxy-dibenzoylmethane, Octocrylene, Ethylhexyl Salicylate, Homosalate, Bemotrizinol | 25.00 | 30.00 |
|  | SymMollient® PDCC | Propylenediol Dicapylate Caprate | 7.00 | 7.00 |
|  | Aristoflex® Silk | Sodium Polyacryloyl-dimethyl Taurate | 0.60 | 0.60 |
|  | KP-545 | Cyclopentasiloxane, Acrylates/Dimethicone Copolymer | 1.00 | 1.00 |
|  | Edeta® BD | Disodium EDTA | 0.10 | 0.10 |
| B | Aqua/Water | Aqua/Water | Ad 100 | Ad 100 |
|  | Symocide® PS | Phenoxyethanol, Caprylyl Glycol | 1.40 | 1.40 |
|  | Glycerin 99% | Glycerin | 2.00 | 2.00 |
|  | Hydrolyte® 5 Green | 1,2-Pentylene Glycol | 2.00 | 2.00 |
| C | Vitacel® CS 20 FC | Cellulose | 1.00 | 1.00 |
|  | Fragrance | Perfume | qs | qs |
|  | In-Vitro SPF |  | 55 | 65 |
|  | In-Vitro UVA PF |  | 19 | 23 |
|  | Critical Wavelength (nm) |  | 379 | 379 |

Manufacturing Procedure

At ambient temperature mix the oils of phase A together with stirring until homogeneous. Then disperse the Aristoflex® and EDTA into the mix. At ambient temperature mix the components of phase B together with stirring until homogeneous and then add with stirring to phase A. Add phase C to phase A/B. Then homogenize with an Ultra Turrax® (13000 rpm/1 minutes per 100 g emulsion).

Example 7

Cold-Cold Manufacture of Sunscreen Balm—Expected SPF 50

| Phase | Ingredient | INCI or USAN name | 7 |
|---|---|---|---|
| A | Aqua/Water | Aqua/Water | Ad 100 |
|  | Neo Heliopan® Hydro | Phenylbenzimidazole Sulfonic Acid | 1.00 |
|  | L-Arginine | Arginine | 0.60 |
|  | Hydrolyte® 5 Green | 1,2-Pentylene Glycol | 2.00 |
|  | SymSave® H | Hydroxyacetophenone | 0.50 |
|  | Hydrolyte® CG | Caprylyl Glycol | 0.25 |
|  | Edeta® BD | Disodium EDTA | 0.10 |
|  | Hyaluronic Acid | Hyaluronic Acid | 0.10 |
|  | Dragosine® | Carnosine | 0.20 |
| B | Aristoflex® Silk | Sodium Polyacryloyldimethyl Taurate | 1.10 |
| C | Blend A | Butyl Methoxy-dibenzoylmethane, Octocrylene, Ethylhexyl Salicylate, Homosalate, Bemotrizinol | 25.00 |
|  | Dragoxat®89 | Ethylxyl Isononanoate | 2.00 |
|  | SymMollient® PDCC | Propylenediol Dicapylate Caprate | 3.00 |
| D | Vitacel® CS 20 FC | Cellulose | 1.00 |
| E | Fragrance | Perfume | qs |
|  | In-Vitro SPF |  | 61 |
|  | In-Vitro UVA PF |  | 30 |

Manufacturing Procedure

Add the first three components of Phase A together with stirring until all of the Neo Heliopan Hydro® has dissolved. Add the rest of the components of phase A together with stirring until the solution get clear. Add phase B with stirring to phase A until a smooth gel has formed. Then add the components of phase C to the gel with stirring. Stir until homogeneous. Then add phase D with stirring, add phase E with stirring and then homogenize for 3 minutes at 10 000 rpm.

Example 8

Hot/Cold-Manufacture of Sunscreen Creams—Expected SPF 50 and 50+

| Phase | Ingredient | INCI or USAN name | 8A | 8B |
|---|---|---|---|---|
| A | Emulsiphos® | Potassium Cetyl Phosphate, Hydrogenated Palm Glycerides | 2.00 | 2.00 |
|  | Blend A | Butyl Methoxy-dibenzoylmethane, Octocrylene, Ethylhexyl Salicylate, Homosalate, Bemotrizinol | 25.00 | 30.00 |
|  | SymMollient® PDCC | Propylenediol Dicapylate Caprate | 6.00 | 6.00 |
|  | Lanette®O | Cetearyl Alcohol | 2.00 | 2.00 |
|  | Cutina® GMS V | Glyceryl Stearate | 1.00 | 1.00 |
|  | Dragoxat®89 | Ethylxyl Isononanoate | 2.00 | 2.00 |
|  | SymMollient®S | Cetearyl Nonanoate | 2.00 | 2.00 |
|  | Keltrol® CC-BT | Xanthan Gum | 0.30 | 0.30 |
|  | Carbopol® Ultrez 21 | Acrylates/C10-30 Alkyl Acrylate Crosspolymer | 0.20 | 0.20 |
|  | Edeta® BD | Disodium EDTA | 0.10 | 0.10 |
| B | Aqua/Water | Aqua/Water | Ad 100 | Ad 100 |
|  | Hydrolyte® 5 Green | 1,2-Pentylene Glycol | 2.00 | 2.00 |
|  | SymSave® H | Hydroxyacetophenone | 0.50 | 0.50 |
|  | Hydrolyte® CG | Caprylyl Glycol | 0.25 | 0.25 |
|  | NaOH 10% aq | Sodium Hydroxide, Water (Aqua) | 0.50 | 0.50 |
| C | Fragrance | Perfume | qs | qs |
|  | In-Vitro SPF |  | 53 | 93 |
|  | In-Vitro UVA PF |  | 20 | 30 |
|  | Critical Wavelength (nm) |  | 379 | 379 |

Manufacturing Procedure

Add all components of phases A together except for the Carbopol® and Keltrol® and heat with stirring to 80° C. Then add the Carbopol® and Keltrol® with stirring. Mix all of the components of phase B at ambient temperature together with stirring until a clear solution has been obtained. Then add to the hot phase A with stirring and homogenize. Allow to cool to room temperature and then add phase C with stirring.

Example 9

Antiaging Sunscreen Lotion (O/W)—Expected SPF 30

| Phase | Ingredient | INCI Name | 9 |
|---|---|---|---|
| A | Emulsiphos ® | Potassium Cetyl Phosphate, Hydrogenated Palm Glycerides | 3.80 |
|  | Lanette ® 16 | Cetyl Alcohol | 1.00 |
|  | Blend A | Butyl Methoxy-dibenzoylmethane, Octocrylene, Ethylhexyl Salicylate, Homosalate, Bemotrizinol | 15.00 |
|  | SymMollient ® PDCC | Propylenediol Dicaprylate Caprate | 5.00 |
|  | SymUrban ® | Benzylidene Dimethoxy-dimethylindanone | 0.50 |
|  | Silsoft ® 034 | Caprylyl Methicone | 3.00 |
|  | Dragoxat ® 89 | Ethylhexyl Isononanoate | 3.00 |
|  | Symsitive ®1609 | Pentylene Glycol, 4-t-Butylcylcohexanol | 1.00 |
|  | Antaron ® WP 660 | Tricontanyl PVP | 1.00 |
|  | EDETA ® BD | Disodium EDTA | 0.10 |
|  | Copherol ® 1250 | Tocopheryl Acetete | 0.50 |
|  | Keltrol ® CG-T | Xanthan Gum | 0.40 |
|  | Wacker-Belsil ® CDM 3526 VP | C26-28 Alkyl Dimethicone | 1.00 |
|  | Hydrolite ®-5 Green | Pentylene glycol | 4.25 |
|  | SymMollient ® S | Cetearyl Nonanoate | 1.00 |
| B | Water | Aqua (Water) | Ad 100 |
|  | Glycerin 99% | Glycerin | 2.00 |
|  | SymSave ® H | Hydroxyacetophenone | 0.50 |
| C | Symdiol ® 68 | 1,2-Hexanediol, Caprylyl Glycol | 0.50 |
|  | Dow Corning ® 9801 Cosmetic Powder | Dimethicone/Vinyl Dimethicone Crosspolymer, Silica | 0.50 |
|  | Fragrance | Perfume | 0.20 |
|  | Dragosantol ® 100 | Bisabalol | 0.10 |
|  | SymGlucan ® | Aqua, Glycerin, Beta-Glucan, 1,2-Hexanediol, Caprylyl Glycol | 1.00 |
|  | Orgasol ®Caresse | Nylon 6/12 | 2.00 |

Manufacturing Procedure

Phase A: Mix the components without Keltrol® T to approx. 85° C. Homogenize for a short time with an Ultra Turrax®. Phase B: Mix the components and heat up to approx. 80° C. until dissolved. Add phase B to phase A while stirring. Cool down while stirring to 60° C. and homogenize with an Ultra Turrax®. Then cool down to ambient temperature while stirring. Phase C: Add all ingredients step by step and stir until homogeneous with an Ultra Turrax®.

Example 10

Sunscreen Spray—Expected SPF 50

| Phase | Ingredient | INCI Name | 10 |
|---|---|---|---|
| A | Dracorin ® GOC | Glyceryl Oleate Citrate, Caprylic/Capric Triglyceride | 2.00 |
|  | Blend A | Butyl Methoxydibenzoyl-methane, Octocrylene, Ethylhexyl Salicylate, Homosalate, Bemotrizinol | 25.00 |
|  | Neo Heliopan ® AV | Ethylhexyl Methoxycinnamate | 2.00 |
|  | SymMollient ® PDCC | Propylenediol Dicapylate Caprate | 7.50 |
|  | Dragoxat ® 89 | Ethylhexyl Isononanoate | 3.00 |
|  | SymMollient ® S | Cetearyl Nonanoate | 2,00 |
|  | EDTA ® BD | Disodium EDTA | 0.10 |
|  | Copherol ® 1250 | Tocopherolacetat-Alpha | 0.50 |
|  | Silcare ® Silicone 41M65 | Stearyl Dimethicone | 1.00 |
|  | Wacker Belsil ® CMD 3526 VP | C26-28 Alkyl Dimethicone | 1.00 |
|  | Silsoft 034 | Caprylyl Methicone | 2.00 |
|  | Pemulen TR 2 | Acrylates/C10-30 Alkyl Acrylate Crosspolymer | 0.20 |
| B | Water, dest. | Water (Aqua) | Ad 100 |
|  | SymSol ® PF-3 | Aqua, Pentylene Glycol, Sodium Lauryl Sulfoacetate, Sodium Oleoyl Sarcosinate, Sodium Chloride, Disodium Sulfoacetate, Sodium Oleate | 3.00 |
|  | Propylenglycol | Propylene Glycol | 5.00 |
|  | EG 56 Polymer Expert | Bis-Methoxy PEG-13 PEG-438/PPG-110 SMDI Copolymer | 0.20 |
|  | SymSave ® H | Hydroxyacetophenone | 0.50 |
| C | Phenoxyethanol | Phenoxyethanol | 0.30 |
|  | SymDiol ® 68 | 1,2 Hexanediol, Caprylylglycol | 0.30 |
|  | Dow Corning ® 1503 | Dimethicone/Dimethiconol | 1.00 |
| D | Tapioca Pure | Tapioca Starch | 1.00 |
|  | Perfume oil | Fragrance (Parfum) | 0.20 |

Manufacturing Procedure

Phase A: Mix the ingredients without Pemulen® TR2 to approx 60° C. with stirring. Add Pemulen® TR2 and homogenize for a short time, approx 0.5 min. with an Ultra Turrax® T25. Phase B: Dissolve ExpertGel® in water while stirring. When dissolved add the rest of the ingredients and stir until a clear solution is obtained. Heat slightly if necessary to solubilize SymSave® H. Add the water phase B without stirring to the warm oil phase A. Homogenize with an Ultra Turrax® for approximately 5 min. Stir to cool down. Phase C: Mix the ingredients stirring and then to phase A/B. Cool down while stirring. Phase D: Add these separately to phases A/B/C with stirring at ambient temperature. Then homogenize for a short time.

Example 11

Water Resistant Broad Spectrum O/W—Expected SPF 50+

| Phase | Ingredients | INCI | 11 |
|---|---|---|---|
| A | Emulsiphos ® | Potassium Cetyl Phosphate, Hydrogenated Palm Glycerides | 3.50 |
|  | Lanette ® O | Cetearylalcohol | 1.00 |
|  | Blend A | Butyl Methoxydibenzoyl-methane, Octocrylene, Ethylhexyl Salicylate, Homosalate, Bemotrizinol | 20.00 |
|  | SymMollient ® PDCC | Propylenediol Dicapylate Caprate | 5.00 |
|  | Abil ® Wax 9801 | Cetyl Dimethicone | 1.00 |
|  | Silcare ® Silicone 41M65 | Stearyl Dimethicone | 1.00 |
|  | Baysilone ® oil PK 20 | Phenyl Trimethicone | 2.00 |
|  | SymMollient ® PDCC | Propylenediol Dicaprylate Caprate | 2.00 |

-continued

| Phase | Ingredients | INCI | 11 |
|---|---|---|---|
|  | Tocopherylacetat | Tocopheryl Acetate | 0.50 |
|  | Antaron ® V216 | VP/Hexadecene Copolymer | 0.50 |
|  | EDTA BD | Disodium EDTA | 0.10 |
|  | Keltrol ® CG-T | Xanthan Gum | 0.50 |
| B | Water dem | Water (Aqua) | Ad 100 |
|  | SymSave ® H | Hydroxyacetophenone | 0.50 |
|  | Lara Care ® A-200 | Galactoarabinan | 0.25 |
|  | Hydrolite ® 5 | Pentylene Glycol | 3.00 |
| C | Fragrance | Perfume | 0.30 |

Manufacturing Procedure

Phase A: Heat all components except for the Xanthan Gum to 85° C. Then add Xanthan Gum and homogenize. Phase B: Heat all components to 85° C. and add to Part A with stirring, stir to room temperature. Phase C: Add Part C to Parts A & B and homogenize.

Example 12

Sunscreen Lotion with Tanning Accelerator—Expected SPF 30

| Phase | Ingredients | INCI-Name | 12 |
|---|---|---|---|
| A | Emulsiphos ® | Potassium Cetyl Phosphate, Hydrogenated Palm Glycerides | 2.00 |
|  | Lanette 16 ® | Cetyl Alcohol | 1.00 |
|  | Blend A | Butyl Methoxy-dibenzoylmethane, Octocrylene, Ethylhexyl Salicylate, Homosalate, Bemotrizinol | 20.00 |
|  | SymMollient ® PDCC | Propylenediol Dicapylate Caprate | 5.00 |
|  | SymUrban ® | Benzylidene Dimethoxy-dimethylindanone | 0.50 |
|  | Dragoxat ® 89 | Ethylhexyl Isononanoate | 3.00 |
|  | SymMollient ® S | Cetearyl Nonanoate | 1.00 |
|  | Dow Corning ® DC 1503 | Dimethicone, Dimethiconol | 0.50 |
|  | Silcare ® Silicone 41M65 | Stearyl Dimethicone | 1.00 |
|  | Silsoft ® 034 | Caprylyl Methicone | 1.50 |
|  | EDETA ® BD | Disodium EDTA | 0.10 |
|  | Vitamin E Acetate | Tocopheryl Acetete | 0.50 |
|  | Keltrol ® CG-T | Xanthan Gum | 0.30 |
|  | Aristoflex ® Velvet | Polyacrylate Crosspolymer-11 | 0.50 |
| B | Water dem | Aqua (Water) | Ad 100 |
| C | Neo Heliopan ® Hydro | Phenylbenzimidazole Sulfonic Acid | 1.50 |
|  | Glycerin 99% | Glycerin | 3.00 |
|  | Dragosine | Carnosine | 0.20 |
|  | Biotive ® L-Arginine | Arginine | 1.00 |
|  | Lanette ® E | Sodium Cetearyl Sulfate | 0.70 |
|  | SymSave ® H | Hydroxyacetophenone | 0.50 |
|  | SymDiol ® 68 | 1,2 Hexanediol, Caprylylglycol | 0.50 |
| D | Fragrance | Perfume | 0.20 |
|  | Tapioca Pure | Tapioca Starch | 2.00 |
|  | SymBronze ® | Caprylic/Capric Triglyceride, Isochryris Galbana Extract | 2.00 |

Manufacturing Procedure

Phase A: Mix ingredients to approx. 85° C. without Keltrol® and Aristoflex®, when all ingredients are dissolved add Keltrol® and Aristoflex® and homogenize with an Ultra Turrax® for a short time. Part B: Mix ingredients with stirring to approximately 80° C. Add the hot phase B to the hot phase A, cool down with stirring to 60° C. and start homogenizing with an Ultra Turrax®. Cool down to ambient temperature while stirring. Part C: Add the ingredients to parts A/B as listed with stirring and allow cooling to ambient temperature. Part D: Add the ingredients with stirring and homogenize for a short time.

Example 13

CC Cream—Expected SPF 50

| Phase | Ingredients | INCI-Name | 13 |
|---|---|---|---|
| A | Cutina ® CP | Cetyl Pamitate | 1.00 |
|  | Tegosoft MM | Myristyl Myristate | 1.00 |
|  | Lanette ® O | Cetearyl Alcohol | 1.00 |
|  | Blend A | Butyl Methoxy-dibenzoylmethane, Octocrylene, Ethylhexyl Salicylate, Homosalate, Bemotrizinol | 25.00 |
|  | SymUrban ® | Benzylidene Dimethoxy-dimethylindanone | 0.30 |
|  | SymMollient ® PDCC | Propylenediol Dicapylate Caprate | 5.00 |
|  | Dragoxat ® 89 | Ethylhexyl Isononanoate | 5.00 |
|  | SymWhite ® 377 | Phenylethyl Resorcinol | 0.20 |
|  | SymRepair ® 100 | Hexyldecanol, Bisabolol, Cetylhydroxyproline Palmitamide, Stearic Acid, Brassica Campestris Sterols | 1.00 |
| A | Symsitive ® 1609 | Pentylene Glycol, 4-t-Butylcylcohexanol | 1.00 |
|  | Dragoxat ® 89 | Ethylhexyl Isononanoate | 2.00 |
|  | Silsoft 034 | Caprylyl Methicone | 3.00 |
|  | Wacker-Belsil ® CDM 3526 VP | C26-28 Alkyl Dimethicone | 1.00 |
|  | EDETA ® BD | Disodium EDTA | 0.10 |
|  | Copherol ® 1250 | Tocopheryl Acetate | 0.50 |
|  | Keltrol ® CG-BT | Xanthan Gum | 0.40 |
|  | Aristoflex ® Velvet | Polyacrylate Crosspolymer-11 | 0.50 |
| B | Water dem | Aqua (Water) | Ad 100 |
|  | Neo Heliopan ® Hydro, | Phenylbenzimidazole Sulfonic Acid | 1.50 |
|  | Glycerin 99% | Glycerin | 4.00 |
|  | Dragosine ® | Carnosine | 0.20 |
|  | SymSol ® PF3 | Aqua, Pentylene Glycol, Sodium Lauryl Sulfoacetate, Sodium Oleoyl Sarcosinate, Sodium Chloride, Disodium Sulfoacetate, Sodium Oleate | 2.50 |
|  | Biotive ® L-Arginine | Arginine | 1.00 |
|  | NaOH 10% aq. | Sodium Hydroxide | 0.30 |
|  | DragoColour ® Brown | Titanium Dioxide (CI 77891), Iron Oxides (CI 77492), Iron Oxides (CI 77491), Iron Oxides (CI 77499) | 2.00 |
|  | SymSave ® H | Hydroxyacetophenone | 0.50 |
| C | SymDiol ® 68 | 1,2 Hexanediol, Caprylylglycol | 0.50 |
| D | Tapioca pure | Tapioca Starch | 2.00 |
|  | Orgasol ® 4000 EXD NAT COS Caresse | Nylon 6/12 | 2.00 |
|  | SymGlucan ® | Aqua, Glycerin, Beta-Glucan, 1,2-Hexanediol, Caprylyl Glycol | 1.00 |
|  | Fragrance | Parfum | 0.20 |

Manufacturing Procedure

Phase A: Mix ingredients to approx. 85° C. without Keltrol®, Aristoflex® when all ingredient are dissolved add Keltrol®, Aristoflex® and homogenize with an Ultra Turrax® for a short time. Phase B: Add the water and neutralization agents Biotive® L-Arginine and the sodium hydroxide solution and stir until homogeneous. Then add the Neo Heliopan® Hydro and stir until all has dissolved. Add the rest of ingredients without Dragocolor® to phase B and heat up to approximately 80° C., add Dragocolor® and homogenize for a short time then add the hot phase B to the hot phase A and start homogenizing with an Ultra Turrax® (13000 rpm/1 minutes per 100 g emulsion). Cool down to ambient temperature while stirring. Part C: Add the ingredients to parts A/B as listed with stirring and allow cooling to ambient temperature. Part D: Add the ingredients with stirring and homogenize for a short time.

Example 14

Sun Protection Sticks—Expected SPFs of 30 and 50+

| Phase | Ingredients | INCI name | 14A | 14B |
|---|---|---|---|---|
| A | Blend A | Butyl Methoxy-dibenzoylmethane, Octocrylene, Ethylhexyl Salicylate, Homosalate, Bemotrizinol | 20.00 | 25.00 |
|  | PCL Liquid 100 | Cetearyl 2-Ethylhexanoate | 0.00 | 5.00 |
|  | SymUrban ® | Benzylidene Dimethoxy-dimethylindanone | 0.50 | 0.50 |
|  | Copherol ® 1250 | Tocopheryl Acetate | 0.70 | 0.70 |
|  | Dracorin ® GOC | Glyceryl Oleate Citrate, Caprylic/Capric Triglyceride | 0.50 | 0.50 |
|  | Lanette ® O | Cetearyl Alcohol | 7.00 | 5.00 |
|  | TeCe-Ozokerit ® N 502 | Ozokerite | 20.00 | 21.00 |
|  | Candenilla Wax LT 281 BI | Candelilla (Euphorbia Cerifera) Wax | 2.00 | 3.00 |
|  | Isoadipate | Diisopropyl Adipate | 5.00 | 2.00 |
|  | Isopropylpalmitat | Isopropyl Palmitate | 8.20 | 3.00 |
|  | PCL Liquid ® 100 | Cetearyl Ethylhexanoate | 2.00 | 5.20 |
|  | SymMollient ® S | Cetearyl Nonanoate | 6.00 | 5.00 |
|  | Wacker Belsil ® CDM 3526 VP | C26-28 Alkyl Dimethicone | 2.00 | 2.00 |
|  | Silcare ® Silicone 41 M45 | Stearyl Dimethicone | 1.00 | 1.00 |
|  | Neutral oil | Caprylic/Capric Triglyceride | Ad 100 | Ad 100 |
|  | SymMollient ® PDCC | Propylenediol Dicaprylate Caprate | 4.00 | 4.00 |
|  | Dragoxat 89 | Ethylhexyl Isononanoate | 2.00 | 1.00 |
|  | Dragosantol ® 100 | Bisabolol | 0.10 | 0.10 |
| B | SymTio ® SP | Titanium Dioxide, Aluminum Hydroxide, Cetearyl Nonanoate | 5.00 | 5.00 |
|  | Zinc Oxide PI | Zinc Oxide | 2.00 | 5.00 |
|  | Dow Corning ® Cosmetic Powder 9701 | Dimethicone/Vinyl Dimethicone Crosspolymer (and) Silica | 2.00 | 2.00 |

Manufacturing Procedure

Phase A: Mix ingredients and heat with stirring to approx. 80° C. Hold the temperature. Phase B: Mix the ingredients then add phase B to phase A and homogenize. Hold the temperature. Stir slowly to let enclosed air escape from the mass. Transfer to the stick holders at 75-80° C.

Example 15

Sunscreen Cream (W/O)—Expected SPF 50, Water Resistant

| Phase | Ingredients | INCI Name | 15 |
|---|---|---|---|
| A | Dehymuls ®PGPH | Polyglyceryl-2 Dipolyhydroxystearate | 5.00 |
|  | Copherol ®1250 | Tocopheryl Acetate | 0.50 |
|  | Permulgin ® 3220 | Ozokerite | 0.50 |
|  | Aluminium stearate | Aluminium Stearate | 0.50 |
|  | Blend A | Butyl Methoxy-dibenzoylmethane, Octocrylene, Ethylhexyl Salicylate, Homosalate, Bemotrizinol | 25.00 |
|  | Tegosoft ® TN | C12-15 Alkyl Benzoate | 5.00 |
|  | Neutral oil | Caprylic/Capric Triglyceride | 5.00 |
|  | SymMollient ® PDCC | Propylenediol Dicaprylate Caprate | 5.00 |
|  | Dragoxat 89 | Ethylhexyl Isononanoate | 5.00 |
|  | EDETA ® BD | Disodium EDTA | 0.10 |
| B | Water, dist. | Water (Aqua) | Ad 100 |
|  | Glycerol, 99% | Glycerin | 4.00 |
|  | SymDiol ® 68 | 1,2 Hexanediol, Caprylylglycol | 0.50 |
|  | SymSave ® H | Hydroxyacetophenone | 0.50 |
|  | Magnesium sulfate | Magnesium Sulfate | 0.50 |
| C | Perfume oil | Perfume | 0.30 |

Manufacturing Procedure

Part A: Mix the ingredients with stirring at about 50° C. Part B: Mix the ingredients with stirring at about 85° C. then add t A. Allow to cool with stirring then homogenize. Part C: Stir in at ambient temperature.

Example 16

Alcoholic Spray—Expected SPF 50

| Phase | Ingredients | INCI Name | 16 |
|---|---|---|---|
| A | Blend A | Butyl Methoxydibenzoylmethane, Octocrylene, Ethylhexyl Salicylate, Homosalate, Bemotrizinol | 30.00 |
|  | Alcohol denat | Alcohol | Ad 100 |
|  | Permulgin ® 3220 | Ozokerite | 0.50 |
|  | Aluminium stearate | Aluminium Stearate | 0.50 |
|  | Butyloctyl Salicylate | Butyloctyl Salicylate | 5.00 |
|  | SymMollient ® PDCC | Propylenediol Dicaprylate Caprate | 5.00 |
|  | Dragoxat 89 | Ethylhexyl Isononanoate | 5.00 |
|  | KP-545 | Cyclopentasiloxane, Acrylates/Dimethicone Copolymer | 1.00 |
|  | Dermacryl ® 79 | Acrylates/Octylacrylamide Crosspolymer | 2.00 |
|  | EDETA ® BD | Disodium EDTA | 0.10 |

-continued

| Phase | Ingredients | INCI Name | 16 |
|---|---|---|---|
| B | Vitamin E Acetate | Tocopheryl Acetate | 2.50 |
|  | Vitamin E | Tocopherol | 0.10 |
|  | Vitamin C Palmitate | Ascorbyl Palmitate | 0.10 |
|  | Vitamin A Palmitate | Retinyl Palmitate | 0.10 |
|  | Magnesium sulfate | Magnesium Sulfate | 0.50 |
| C | Perfume oil | Perfume | 0.30 |

Manufacturing Procedure

Part A: Disperse the Dermacryl and KP-545 into the alcohol and then mix in the other ingredients with stirring at about 50° C. and cool to ambient temperature. Part B: Mix the ingredients with stirring at ambient temperature then add to A with stirring then homogenize. Part C: Stir in at ambient temperature Example 17

Antiaging Facial Lotion (O/W)—Expected SPF>50

| Phase | Ingredients | INCI Name | 17 |
|---|---|---|---|
| A | Glyceryl Stearate | Glyceryl Stearate | 3.00 |
|  | PEG-100 Stearate | PEG-100 Stearate | 1.00 |
|  | Blend A | Butyl Methoxydibenzoylmethane, Octocrylene, Ethylhexyl Salicylate, Homosalate, Bemotrizinol | 25.00 |
|  | Corapan ® TQ (182585) | Diethylhexyl 2,6-Naphthalate | 2.00 |
|  | SymMollient ® PDCC | Propylenediol Dicaprylate Caprate | 5.00 |
|  | SunSpheres ™ Powder | Styrene/Acylates Copolymer | 2.00 |
|  | Pemulen ™ TR-2 | Acrylates/C10-30 Alkyl Acrylate Crosspolymer | 1.00 |
|  | KP-545 | Cyclopentasiloxane, Acrylates/Dimethicone Copolymer | 1.00 |
|  | Silica | Silica | 5.00 |
|  | Beeswax | Cera Alba | 3.00 |
|  | EDETA ® BD | Disodium EDTA | 0.10 |
| B | Water | Aqua (Water) | Ad 100 |
|  | Ethylhexyl Glycerin | Ethylhexyl Glycerin | 1.00 |
|  | Chlorphenesin | Chlorphenesin | 0.50 |
|  | BHT | Butyl Hydroxytoluene | 0.10 |
|  | Dipotassium glycyrrizate | Dipotassium glycyrrizate | 0.10 |
| C | Dragosantol ® 100 | Bisabalol | 0.10 |
|  | SymGlucan ® | Aqua, Glycerin, Beta-Glucan, 1,2-Hexanediol, Caprylyl Glycol | 1.00 |
|  | Fragrance | Perfume | 0.20 |

Manufacturing Procedure

Phase A: Mix the components without silica and Pemulen to approx. 85° C., then add the other parts. Homogenize for a short time with an Ultra Turrax®. Phase B: Mix the components and heat up to approx. 50° C. until dissolved. Add phase B to phase A while stirring. Cool down while stirring to 30° C. and homogenize with an Ultra Turrax®. Then cool down to ambient temperature while stirring. Phase C: Add all ingredients step by step and stir until homogeneous with an Ultra Turrax®.

What is claimed is:

1. A liquid and transparent blend of UV filters, of
   (a) at least one solid UVA filter dissolved in
   (b) at least one liquid UVB filter,
   said blend comprising
   (a1) about 9 to about 15 wt.-% avobenzone,
   (a2) about 12 to about 25 wt.-% bemotrizinol,
   (b1) about 20 to about 35 wt.-% octocrylene,
   (b2) about 9 to about 15 wt.-% octisalate, and
   (b3) about 9 to about 15 wt.-% homoslate,
   on condition the amounts add to 100 wt.-%.

2. A cosmetic, dermatological or pharmaceutical composition comprising the liquid and transparent blend of UV filters according to claim 1.

3. The composition of claim 2, further comprising at least one additional UVA filter selected from the group consisting of:
   terephthalylidenedibornanesulphonic acid and salts;
   hexyl 2-(4-diethylamino-2-hydroxybenzoyl)benzoate;
   menthyl anthranilate;
   2,2'-(1,4-phenylene)bis-[1H-benzimidazole-4,5-disulfonic acid], disodium salt, and mixtures thereof.

4. The composition of claim 2, further comprising at least one additional UVB filter selected from the group consisting of:
   2-ethylhexyl p-dimethylaminobenzoate;
   triethanolamine salicylate;
   2-ethylhexyl p-methoxycinnamate;
   isoamyl p-methoxycinnamate;
   2-phenylbenzimidazole sulfonic acid and its salts;
   3-(4'-methylbenzylidene)-d,l-camphor;
   4,4'-[(6-[4-(1,1-dimethyl)aminocarbonyl)phenylamino]-1,3,5-triazine-2,4-diyl)diimino]bis(benzoic acid 2-ethylhexyl ester);
   benzylidenemalonate-polysiloxane;
   tris(2-ethylhexyl)4,4',4"-(1,3,5-triazine-2,4,6-triyl-triimino)tribenzoate);
   methoxy propylamino cyclohexenylidene ethoxyethyl cyanoacetate;
   and mixtures thereof.

5. The composition of claim 2, further comprising at least one additional broadband filter selected from the group consisting of:
   2-hydroxy-4-methoxybenzophenone-5-sulfonic acid or its salts;
   2-hydroxy-4-methoxybenzophenone;
   phenol,-(2H-benzotriazol-2-yl-4-methyl-6-(2-methyl-3-(1,3,3,3-tetramethyl-1-(trimethylsilyl)oxy)disiloxanyl)propyl);
   2,2'-methylenebis(6-(2H-benztriazol-2-yl)-4-1,1,3,3-tetramethylbutyl)-phenol;
   tris-biphenyl triazine;
   (5,6,5',6'-tetraphenyl-3,3'-(1,4-Phenylene)bis(1,2,4-triazine 5,6,5',6'-tetraphenyl-3,3'-(1,4-phenylene)bis(1,2,4-triazine);
   and mixtures thereof.

6. The composition of claim 2, further comprising at least one pigment selected from the group consisting of zinc oxide, titanium dioxide and mixtures thereof.

7. The composition of claim 2 exhibiting a sun protection factor (SPF) of at least 2.

8. The composition of claim 2, exhibiting a UVA protection factor of at least 370 nm, as measured by the Critical Wavelength Method for in vitro determination of UVA protection.

9. The composition of claim 2, exhibiting a UVA protection factor of at least one third of the SPF, as measured by ISO norm 24443:2012 for vitro determination of UVA protection.

10. The composition of claim 2, further comprising at least one 1,2-alkanediol having 5 to 12 carbon atoms.

11. The composition of claim 2, further comprising 4-hydroxyacetophenone, o-cymen-5-ol or mixtures thereof.

12. The composition of claim 2 which is photostable.

13. The composition of claim 2, wherein the composition is an oil in water emulsion.

14. The composition of claim 2, wherein the composition is a water in oil emulsion.

15. The composition of claim 2 representing an alcoholic spray.

16. The composition of claim 2, further comprising emulsifiers selected from the group consisting of alkyl phosphates, glyceryl oleate citrates, glycereyl stearate citrates, stearic acid esters, sorbitan esters, ethoxylated sorbitan esters, ethoxylated mono-, di- and tri glycerides, methyl glucose esters, and mixtures thereof.

17. The composition of claim 16, wherein the amount of emulsifier is in the range of about 1 to about 10 percent by weight, related to the composition.

18. The composition of claim 2 being obtained from a hot/hot, or cold/hot, or hot/cold or cold/cold manufacturing processes.

19. A non-therapeutic method for protecting human skin and hair against UV radiation comprising the following steps:
  (i) providing the blend of claim 1, and
  (ii) bringing said blend in contact with said human skin or hair.

20. The composition of claim 14, wherein said emulsion encompasses an oil phase comprising additives selected from the group consisting of hydrocarbon oils, waxes, silicone oils, natural oils, fatty acid esters, fatty alcohols, antioxidants, chelating agents, skin lightening agents, tan accelerating agents, insect repelling agents, moisturizing agents, water resistant polymers, and mixtures thereof.

21. The composition of claim 14, wherein said emulsion encompasses an aqueous phase comprising additives selected from the group consisting of antioxidants, preservation agents, chelating agents, and mixtures thereof.

22. A liquid and transparent blend of UV filters, consisting of
  (a) 13.5 wt.-percent butyl methoxydibenzoylmethane,
  (b) 27.0 wt.-percent octocrylene,
  (c) 27.0 wt.-percent homosalate,
  (d) 13.5 wt.-percent octisalate, and
  (e) 19.0 wt.-percent bemotrizinol.

* * * * *